United States Patent [19]
Gould-Fogerite et al.

[11] Patent Number: 5,994,318
[45] Date of Patent: *Nov. 30, 1999

[54] COCHLEATE DELIVERY VEHICLES

[75] Inventors: Susan Gould-Fogerite; Raphael James Mannino, both of Annandale, N.J.

[73] Assignees: Albany Medical College, Albany, N.Y.; University of Medicine and Dentistry of New Jersey, Newark, N.J.

[*] Notice: This patent is subject to a terminal disclaimer.

[21] Appl. No.: 08/803,662

[22] Filed: Feb. 21, 1997

Related U.S. Application Data

[63] Continuation-in-part of application No. PCT/US96/01704, Feb. 22, 1996, which is a continuation-in-part of application No. 08/394,170, Feb. 22, 1995, Pat. No. 5,840,707, which is a continuation-in-part of application No. 08/130,986, Oct. 4, 1993, Pat. No. 5,643,574.

[51] Int. Cl.$^6$ .................................................. H61K 48/00
[52] U.S. Cl. ..................................... 514/44; 514/2; 514/8; 435/458; 424/88; 424/401; 424/450; 424/184.1; 424/121; 264/4.6
[58] Field of Search ................................ 424/184.1, 121, 424/88, 401, 450; 264/4.6; 514/8, 44, 2; 435/458

[56] References Cited

U.S. PATENT DOCUMENTS

| | | | |
|---|---|---|---|
| 4,078,052 | 3/1978 | Papahadjopoulos | 424/36 |
| 4,663,161 | 5/1987 | Mannino et al. | 424/89 |
| 4,725,442 | 2/1988 | Haynes | 424/490 |
| 4,871,488 | 10/1989 | Mannino et al. | 264/4.6 |
| 4,874,795 | 10/1989 | Yesair | 514/725 |
| 4,906,476 | 3/1990 | Radhakrishnan | 424/450 |
| 5,026,557 | 6/1991 | Estis | 424/450 |
| 5,190,760 | 3/1993 | Baker | 424/438 |
| 5,409,698 | 4/1995 | Anderson | 424/85.2 |
| 5,484,589 | 1/1996 | Salganik | 424/94.2 |
| 5,529,914 | 6/1996 | Hubbell et al. | 435/182 |
| 5,571,517 | 11/1996 | Yesair | 514/725 |
| 5,580,859 | 12/1996 | Felgner et al. | 514/44 |
| 5,589,466 | 12/1996 | Felgner et al. | 514/44 |
| 5,603,931 | 2/1997 | Raso | 424/136.1 |
| 5,612,019 | 3/1997 | Gordon et al. | 424/9.32 |

OTHER PUBLICATIONS

Booser et al., Anthracycline antibiotics in cancer therapy. Drugs 47:223–258, 1994.
Mori et al., Immunotargeting of liposomes containing lipophilic antitumor prodrugs. Pharmaceutical 10:507–514, 1993.
Liposome Technology, 2nd Ed., vol. 1, G. Gregoriadis, "Liposome preparation and related techniques" published 1993 by CRC Press, Inc., (Boca Raton), pp. 67–80.
Miller et al., Vaccination of Rhesus monkeys with synthetic peptide in a fusogenic proteoliposome elicits simian immunodeficiency virus–specific CD8+ cytotoxic T lymphocytes. J.Exp.Med. 176:1739–1744, 1992.
Deres et al., In vivo priming of virus–specific cytotoxic T lymphocytes with synthetic lipopeptide vaccine. Nature 342:561–564, 1989.
Gould–Fogerite et al., Chimerasome–mediated gene transfer in vitro and in vivo. Gene 84:429–438, 1989.
Papahadjopoulos et al., Cochleate lipid cylinders: formation by fusion of unilamellar lipid vesicles. Biochimica et Biophysica Acta 394:483–491, 1975.
Gould–Fogerite et al., Rotary dialysis: its application to the preparation of large liposomes and large proteoliposomes (protein–lipid vesicles) with high encapsulation efficiency abd efficient reconstitution of membrane proteins. Analytical Biochem. 148:15–25, 1985.
Kim et al., Advances in membrane biochemistry and bioenergetics, published 1988 by Plenum Publishing Corporation, pp. 569–586.
R.J. Mannino and S. Gould–Fogerite, Liposome mediated gene transfer. BioTechniques 6:682–690, 1988.
Gould–Fogerite et al., The reconstitution of biologically active glycoproteins into large liposomes: use as a delivery vehicle to animal cells. Advances in Membrane Biochemistry and Bioenergetics, pp. 569–586, 1988.
Gould–Fogerite and Mannino, Liposome preparation and related techniques. Liposome Technology 2nd Ed., vol. I, pp. 67–80.
Gould–Fogerite and Mannino, Entrapment of drugs and other materials. Liposome Technology 2nd Ed., vol. II, pp. 167–184.
Gould–Fogerite and Mannino, Interaction of liposomes with the biological milieu. Liposome Technology 2nd Ed., vol. III, pp. 261–276.
Goodman–Snitkoff et al., Defining minimal requirements for antibody production to peptide antigens. Vaccine 8:257–262, 1990.
Goodman–Snitkoff et al., Role of intrastructural/intermolecular help in immunization with peptide–phospholipid complexes. J.Immunol. 147:410–415, 1991.
Krowka, J.Immunol. 144:2535, 1990.
Wassely, Immunol.Methods 4:217, 1994.
Oleske et al., Autogenous vaccine treatment of laryngeal papilloma. Curr.Chemotherapy and Immunotherapy, Proc. 12th Intl. Cong. of Chemotherapy, Florence, Italy, Jul. 19–24, 1981, pp. 1099–1101.
Oleske et al., Juvenile papilloma of the larynx, Am.J. of Diseases of Children 121:417–419, 1971.

(List continued on next page.)

*Primary Examiner*—Bruce R. Campell
*Assistant Examiner*—Dave Trong Nguyen
*Attorney, Agent, or Firm*—Sughrue, Mion, Zinn, Macpeak & Seas, PLLC

[57] ABSTRACT

The instant disclosure relates to cochleates comprising a) a biologically relevant molecule component b) a negatively charged lipid component, and c) a divalent cation component. The cochleate has an extended shelf life, even in a desiccated state. Advantageously, the cochleate can be ingested. The biologically relevant molecule can be a topical application and an in vitro treatment, a polypeptide a drug, a nutrient, or a flavor.

59 Claims, 9 Drawing Sheets

OTHER PUBLICATIONS

Kensil et al., Structure/function relationship in adjuvants from Quillaja saponaria Molina, Vaccines 92, Cold Spring Harbor Laboratory Press, 1992, pp. 35–40.

Kensil et al., The use of stimulation adjuvant to boost vaccine response, Vaccine Research, 2:273–281, 1993.

Newman et al., Immunogenicity and toxicity testing of an experimental HIV–1 vaccine in nonhuman primates. AIDS research and human retroviruses 8:1413–1418, 1992.

Wu et al., Accesory cell requirements for saponin adjuvant–induced class I MHC antigen–restricted cytotoxic T–lymphocytes. Cell.Immunol. 154:393–406, 1994.

Wu et al., Saponin adjuvant enhancement of antigen–specific immune responses to an experimental HIV–1 vaccine. J.Immunol. 148:1519–1525, 1992.

Newman et al., Saponin adjuvant induction of ovalbumin–specific CD8+ cytotoxic T lymphocyte responses J.Immunol. 148:2357–2362, 1992.

Kensil et al., Separation and characterization of saponins with adjuvant activity from Quillaja saponaria Molina cortex. J.Immunol. 146:431–437, 1991.

Salk, Contakos et al., Use of adjuvants in studies on influenza immunization, J.A.M.A. 151:1169–1175, 1953.

Graham et al., Augmentation of human immunodeficiency virus type 1 neutralzing antibody by printing with gp160 recombinant vaccinia and boosting with rgp160 in vaccinia–naive adults. J.Infect.Dis. 167:533–537, 1993.

Celis et al., Regulation of the human immune response to HBsAg: effects of antibodies and antigen conformation in the stimulation of helper T cells by HBsAg. Hepatology 5:744–751, 1985.

Salk, Prospects for the control of AIDS by immunizing seropositive individuals. Nature 327:473–476, 1987.

Bisaccia et al., Extracorporeal photopheresis in the treatment of AIDS–related complex: a pilot study Annals of Internal Medicine 113:270–275, 1990.

Lanzavecchia et al., T cells can present antigens such as HIV gp120 targeted to their own surface molecules. Nature 334:530–534, 1988.

McDougal et al., Antibody response to human immunodeficiency virus in homosexual men. J.Clin.Invest. 80:316–324, 1987.

Belshe et al., Safety and immunogenicity of a fully glycosylated recombinant gp160 human immunodeficiency virus type 1 vaccine in subjects at low risk of infection. J. Infect. Dis. 168:1387–1395, 1993.

Walker et al., HIV–specific cytotoxic T lymphocytes in seropositive individuals. Nature 328:345–348, 1987.

Stanhope et al., Human CD4+ cytolytic T lymphocyte responses to a human immunodeficiency virus type 1 gp160 subunit vaccine. J.Infect.Dis. 168:92–100, 1993.

Beretta et al., HIV env glycoprotein shares a cross–reacting epitope with a surface protein present on activated human monocytes and involved in antigen presentation. Eur.J.Immunol. 17:1793–1798, 1987.

Golding et al., Common epitope in human immunodeficiency virus (HIV) I–GP41 and HLA Class II elicits immunosuppressive autoantibodies capable of contributing to immune dysfunction in HIV I–infected individuals. J. Clin. Invest. 83:1430–1435, 1989.

De Santis et al., Cross–reactive response to human immunodeficiency virus type 1 (HIV–1) gp120 and HLA Class I heavy chains induced by receipt of HIV–1 derived envelope vaccines. J.Infect.Dis. 168: 1396–1403, 1993.

Redfield et al., Psoralen inactivation of influenza and herpes simplex viruses and of virus–infected cells. Infect.Immun. 32:1216–1226, 1981.

Livingston et al., Approaches to augmenting the IgG antibody response to melanoma ganglioside vaccines. Annals New York Academy of Sciences, pp. 204–213.

Gold et al., Viagene begins new gene therapy trial. Treatment Issues 8:5–13.

Darrow et al., Immunotherapy of human melanoma with gene–modified tumor cell vaccines. Cancer Control pp. 415–428, Sep./Oct. 1995.

Wain–Hobson, Virological Mayhem, News and Views.

Bernengo et al., The in vitro effect of calf thymus extract on the peripheral blood lymphocytes of patients with warts. British J.Derm. 102:11–16, 1980.

Ingimarsson et al., Side effects of long–term treatment with human leukocyte inteferon. J.Infect.Dis. 140:560–563, 1979.

Scott et al., Effect of injections of small doses of human fibroblast interferon into genital warts. British J. Venereal Diseases 55:442–445, 1979.

Soltysik et al., Adjuvant activity of QS–21 isomers. Annals of the New York Academy of Sciences 690: 392–395, 1993.

White et al., A purified saponin acts as an adjuvant for a T–independent antigen. Immunobiol. of proteins and peptides VI, pp. 207–210, 1991.

Kensil et al., Novel adjuvants from Quillaja saponaria Molina, AIDS Research Review 3:379–389, 1993.

Van Damme et al., Simultaneous production of interleukin 6, interferon–beta and colony–stimulating activity by fibroblasts after viral and bacterial infection. Eur.J.Immunol. 19:163–168, 1989.

Sehgal et al., Regulation of acute phase and immune responses in viral disease. Enhanced expression the beta–2 interferon/hepatoxyte–stimulating factor/interleukin 6 gene in virus–infected human fibroblasts. J.Exp.Med. 167:1951–1956, 1988.

Garman et al., Characterization of helper factors distinct from interleukin 2 necessary for the generation of allospecific cytolytic T lymphocytes. J.Immunol. 130:756–762, 1983.

Roberts, Different effects of influenza virus, respiratory syncytial virus, and sendai virus on human lymphocytes and macrophages. Infect.Immun. 35:1142–1146, 1982.

Prujansky–Jakobovits et al., Alteration of lymphocyte surface properties by insertion of foreign functional components of plasma membrane. Proc.Nat'l.Acad.Sci. 77:7247–7251, 1980.

Leung et al., Selective suppression of the cytotoxic T cell response to influenza virus in mice. Eur. J.Immunol. 10:803–810, 1980.

Fukami et al., Difference in capacity of Sendai virus envelope components to induce cytotoxic T lymphocytes in prmary and secondary immune response. Infect.Immun. 26:815–821, 1979.

Megyeri et al., Stimulation of interferon and cytokine gene expression by Imiquimod and stimulation by Sendai virus utilize similar signal transduction pathways. Mol.Cell.Biol. 15:2207–2218, 1995.

Hou et al., Hostresponse to Sendai virus in mice lacking Class II Major Histocompatibility Complex glycoporteins. J.Virol. 69:1429–1439, 1995.

Mo et al., Induction of cytokines in mice with Parainfluenze pneumonia. J.Virol. 69:1288–1291, 1995.

Hou, Divergence between cytotoxic effector function and tumor necrosis factor alpha production for inflammatory CD4+ T cells from mice with Sendai virus pneumonia. J.Virol. 67:6299–6302, 1993.

D'Addario et al., Coordinate enhancement of cytokine gene expression in human immunodeficiency virus type 1–infected promonocytic cells. J.Virol. 64:6080–6089, 1990.

Sueishi et al., Effects of cytokines from virus–induced human lymphoblasts on the growth and viability of the promyelocytic leukemia cell line HL–60. J.Interferon Res. 10:379–383, 1990.

Ray et al., Activation of human "beta 2–interferon/hepatocyte–stimulating factor/interleukin 6" promoter by cytokines, viruses, and second messenger agonists. Proc.Nat'l.Acad.Sci. 85:6701–6705, 1988.

Bollon et al., Human cytokines, tumor necrosis factor, and interferons: gene cloning, animal studies, and clinical trials. J.Cell.Biochem. 36:353–367, 1988.

Wabuke–Bunoti et al., Stimulation of anti–influenza cytolytic T lymphocytes by a synthetic peptide of influenza hemagglutinin can be modulated by at least three independent helper factors. J.Immunol. 133:2186–2193, 1984.

Taku et al., A helper factor needed for the generation of mouse cytolytic T lymphocytes is made by tumor cell lines, cloned T cells, and spleen cells exposed to a variety of stimuli. J.Immunol. 133: 502–508, 1984.

Garman et al., Chromatographic separation from known cytokines of a helper factor necessary for the generation of murine cytolytic T lymphocytes. J.Immunol. 132:1879–1887, 1984.

Dehlin et al., Repression of beta interferon gene expression in virus–infected cells is correlated with a Poly(A) tail elongation. Mol.Cell.Biool. 16:468–474, 1996.

Aboagye–Matheisen et al., production of interferons in human placental trophoblast subpopulations and their possible roles in pregnancy. Clin.Diagn.Lab.Immunol. 1:650–659, 1994.

Dejucq et al., Interferon–alpha and –gamma expression in the rat testis. Endocrinology 136:4925–4931, 1995.

Dipaola et al., Interferon–alpha 2 produced by normal human leukocytes is predominantly interferon–alpha 2b. J. Interferon Res. 14:325–332, 1994.

Mo et al., Induction of cytokines in mice with Parainfluenza pneumonia. J.Virol. 69:1288–1291, 1995.

King et al., The beta–interferon promoter responds to priming through multiple independent regulatory elements. J.Biol.Chm. 269:30609–30615, 1994.

Ellis et al., NF–kappa B–independent activation of beta–interferon expression in mouse F9 embryonal carcinoma cells. Nucleic Acids Res. 22:4489–4496, 1994.

Katschinski et al., Influenc of various factors on interferon–alpha production in cultures of human leukocytes. J.Interferon Res. 14:105–110, 1994.

Feldman et al., Viral induction of low frequency interferon–alpha producing cells, Virol. 204:1–7, 1994.

Mori et al., A high–level and regulatable production system for recombinant glycoproteins using a human interferon–alpha promoter–based expression vector. Gene 144:289–293, 1994.

Garoufalis et al., Viral induction of the human beta interferon promoters modulation of transcription by NK–kappa B/Rel proteins and interferon regulatory factors. J.Virol. 68:4707–4715, 1994.

Roulston, Virus induction of NF–kappa B/Rel proteins and type I inter gene expression in myelomono–blastic cells. Leukemia 8:S170–174, 1994.

Aboagye–Mathiesen et al., Human trophoblast interferons. Antiviral Res. 22:91–105, 1993.

Roulston, Chronic human immunodeficiency virus type i intection stimulates distinct NF–kappa B/Rel DNA binding activities in myelomonoblastic cells. J.Virol. 67:5235–5246, 1993.

Rosztoczy et al., Priming does not change promoter sequence requirements for IFN induction or correlate with the expression of IFN regulatory factor–1. J.Immunol. 151:1303–1311, 1993.

Zoon et al., Purification and characterization of multiple components of human lyphoblastoid interferon–alpha. J.Biol.Chem. 267:15210–15216, 1992.

Toth et al., interferon production by cultured human trophoblasts and choriocarcinoma cell lines induced by Sendai virus. J.Gen.Virol. 71 (Pt. 12):3067–3069, 1990.

Busam et al., Virus vs. endotoxin–induced activation of liver macrophages. Eur.J.Biochem. 191:577–582, 1990.

Hiscott et al., Inductionof human interferon gene expression is associated with a nuclear factor that interacts with the NF–kappa B site of the human immunodeficiency virus enhancer. J.Virol. 63:2557–2566, 1989.

Brownstein et al., Immunostimulation in mice infected with Sendai virus. Am.J.Vet.Res. 48:1692–1696, 1987.

Aderka et al., Tumor necrosis factor induction by Sendai virus. J.Immunol. 136:2938–2942, 1986.

Neame et al., A simple methodology for the routine production and partial purification of human lymphoblastoid interferon. Adv.Exp.Med.Biol. 172:269–279, 1984.

Ito et al., Components of Sendai virus that can induce interferon in mouse sleen cells. Infect. Immun. 39:1019–1023, 1983.

Zhou, Characterization of TAP–independent and brefeldin A–resistant presentation of Sendai virus antigen to CD8+ cytotoxic T lymphocytes. Scand. J. Immunol. 42:66–75, 1995.

Liu et al., Heat–inactivated Sendai virus can enter multiple MHC Class I processing pathways and generate cytotoxic T lymphocyte responses in vivo. J.Immunol. 154:3147–3155, 1995.

Hou et al., Host response to Sendai virus in mice lacking Class II Major Histocompatibility Complex glycoproteins. J.Virol. 69:1429–1434, 1995.

Ewing et al., Virus–specific CD8+ T–cell responses in mice transgenic for a T–cell receptor beta chain selected at random. J.Virol. 68:3065–3070, 1994.

Zhounet et al., Antigen processing mutant T2 cells present viral antigen restricted through H–2Kb. Eur. J. Immunol. 23:1802–1808, 1993.

Zhou et al., TAP2–defective RMA–S cells present Sendai virus antigen to cytotoxic T lymphocytes. Eur.J.Immunol. 23:1796–1801, 1993.

Hou et al., Delayed clearance of sendai virus in mice lacking Class I MHC–restricted CD8+ T cells. J.Immunol. 149:1319–1325, 1992.

Harris et al., Antigen recognition by H–2 restricted cytolytic T lymphocytes is not mediated by two independent receptors. J.Exp.Med. 159:330–335, 1984.

Harris et al., Direct transfer of antigen–specific cytolytic activity to noncytolytic cells upon fusion with liposomes derived from cytolytic T cell clones. J.Exp.Med. 159:261–275, 1984.

Hale et al., Elicitation of anti–H–2 cytotoxic T lymphocytes with antigen–modified H–2 negative stimulator cells. J.Immunol. 126:1485–1488, 1981.

McGee et al., Elicitation of primary anti–sendai virus cytotoxic T lymphocytes with purified viral glycoproteins. Eur. J.Immunol. 10:923–928, 1980.

Hale et al., Antigen–liposome modification of target cells as a method to alter their susceptibility to lysis by cytotoxic T lymphocytes. Proc.Nat'l.Acad.Sci. 77:6105–6108, 1980.

Halr et al., Elicitation of anti–viral cytotoxic T lymphocytes with purified viral and H–2 antigens. J.Immunol. 125:428–430, 1980.

Kaszinowski, recognition of viral glycoproteins by influenza A–specific cross–reactive cytolytic T lmphocytes. J.Exp/Med. 151:945–958, 1980.

Hale et al., Minimal molecular requirements for reactivity of tumor cells with T cells. J.Immunol. 124:2063–2070, 1980.

Hale et al., Elicitation of anti–sendai virus cytotoxic T lymphocytes by viral and H–2 antigens incorporated into the same lipid bilayer by membrane fusion and by reconstitution into liposomes. J.Immunol. 124:724–732, 1980.

Finberg et al., The induction of virus–specific cytotoxic T lymphocytes with solubilized viral and membrane proteins. J.Exp.Med. 148:1620–1627, 1978.

Cohen, Bumps on the vaccine road. Science 265:1371–1373, 1994.

Cohen, Are researchers racing toward success or crawling? Science 265:1373–1375, 1994.

Nowak, U.S. national program is going nowhere fast. Science 265:1375–1376, 1994.

Gibbons, Children's vaccine initiative stumbles. Science 265:1376–1377, 1994.

Bloom, The United States needs a national vaccine authority. Science 265:1378–1380, 1994.

Nussenzweig and Long, Malarial vaccines: multiple targets. Science 265:1381–1383, 1994.

Plotkin, Vaccines for Varicella–Zoster virus and cytomegalovirus: recent progress. Science 265:1383–1385, 1994.

Siber, Pneumococcal disease: prospects for a new generation of vaccines. Science 265:1385–1387, 1994.

Mekalanos and Sadoff, Cholera vaccines: fighting an ancient scourge. Science 265:1387–1389, 1994.

Hale et al., Elicitation of anti–sendai virus cytotoxic T lymphocytes by viral and H–2 antigens incorporated into the same lipid bilayer by membrane fusion and by reconstitution into liposome Katz et al., Measles vaccine: do we need new vaccines or new programs? Science 265:1391–1392, 1994.

Hall, Prospects for a respiratory syncytial virus vaccine. Science 265:1393=1394, 1994.

Sprent et al., Lymphocyte life–span and memory. Scince 265:1395–1400, 1994.

Rabinovich et al., Vaccine technologies: view to the future. Science 265:1401–1404, 1994.

J. Immunol. 124:724–732, 1980.

COCHLEATE DELIVERY VEHICLES

This is a continuation-in-part of PCT US/96/01704 filed Feb. 22, 1996, which is a continuation-in-part of application Ser. No. 08/394,170 filed Feb. 22, 1995, now U.S. Pat. No. 5,840,707, which is a continuation-in-part of application Ser. No. 08/130,986 filed Oct. 4, 1993.

Portions of the subject matter disclosed herein were supported in part by monies or grants from the United States Government.

FIELD OF THE INVENTION

The instant invention relates to cochleates and use thereof to stabilize biologic molecules, such as carbohydrates, vitamins, minerals, polynucleotides, polypeptides, lipids and the like. Cochleates are insoluble stable lipid-divalent cation structures into which is incorporated the biologic molecule. Because cochleates can be biologically compatible, cochleates can be administered to hosts by conventional routes and can serve to deliver the biologic molecule to a targeted site in a host.

BACKGROUND OF THE INVENTION

Plain lipid cochleates (FIG. 1) have been described previously. Protein-cochleates or peptide-cochleates have been described heretofore and patented by the instant inventors, as intermediate structures which can be converted to protein-lipid vesicles (proteoliposomes) (FIG. 2) by the addition of calcium chelating agents (see U.S. Pat. No. 4,663,161 and U.S. Pat. No. 4,871,488, the disclosures of which expressly are incorporated herein by reference). Freeze-fracture electron micrographs of protein-(cochleates containing Sendai glycoproteins made by the DC method show the rolled up lipid bilayer structures with a "bumpy" surface. Plain phospholipid cochleates are smooth in that type of preparation.

The proteoliposomes resulting from polypeptide-cochleates have been shown to be effective immunogens when administered to animals by intraperitoneal and intramuscular routes of immunization (G. Goodman-Snitkoff, et al., *J. Immunol.*, Vol. 147, p.410 (1991); M. D. Miller, et al., *J. Exp. Med.*, Vol. 176, p. 1739 (1992)). Further, when the glycoproteins of Sendai or influenza virus are reconstituted by that method, the proteoliposomes are effective delivery vehicles for encapsulated proteins and DNA to animals and to cells in culture (R. J. Mannino and S. Gould-Fogerite, *Biotechniques*, Vol. 6, No. 1, pp. 682–690 (1988); S. Gould-Fogerite et al., Gene, Vol. 84, p. 429 (1989); M. D. Miller, et al., *J. Exp. Med.*, Vol. 176, p. 1739 (1992))

It would be advantageous to provide a means for stabilizing or preserving biologic molecules in a form that is stable at room temperature, capable of desiccation and is suitable for oral administration. For example, it would be beneficial to have a formulation for stabilizing polynucleotides and which could be used for delivering polynucleotides to a cell. A formulation comprised of drugs, nutrients and flavors would also be beneficial for the stabilization and delivery of the molecules to a cell.

SUMMARY OF THE INVENTION

Accordtingly, it is an object of the instant invention to provide a means for stabilizing biologic molecules to yield a formulation with prolonged shelf life, which can be made into powder form and which later can be rehydrated to yield a biologically active molecule.

It also is an object of the instant invention to provide a formulation suitable for use as a vehicle to administer a biologically active molecule to a host. The formulation can be used to deliver a biologic molecule to the gut for absorption or to a targeted organ, tissue or cell. A suitable biologic molecule is a polynucleotide or a bioactive compound such as a lipophilic drug.

Other suitable biologic molecules are polypeptides such as hormones and cytokines or nutrients such as vitamins, minerals, and fatty acids.

Yet other suitable biologic molecules are essential oils which impart flavor.

Those and other objects have been obtained by providing a cochleate formulation comprising the following components:

a) at least one biologically relevant molecule component to be stabilized or delivered, b) at least one negatively charged lipid component, and c) at least one divalent cation component.

In a preferred embodiment, the cochleate formulation is administered orally.

The instant invention further provides a cochleate formulation containing a polynucleotide wherein said polynucleotide-cochleate comprises the following components:

a) at least one polynucleotide component, b) at least one negatively charged lipid component, and c) at least one divalent cation component.

The polynucleotide can be one which is expressed to yield a biologically active polypeptide or polynucleotide. Thus, the polypeptide may serve as an immunogen or, for example, have enzymatic activity. The polynucleotide may have catalytic activity, for example, be a ribozyme, or may serve as an inhibitor of transcription or translation, that is, be an antisense molecule If expressed, the polynucleotide would include the necessary regulatory elements, such as a promoter, as known in the art.

The instant invention further provides a cochleate formulation containing a polypeptide, wherein said polypeptide-cochleate comprises the following components:

a) a polypeptide component b) a negatively charged lipid component, and c) a divalent cation component.

A specific example is an insulin cochleate.

The instant invention also provides a cochleate formulation containing a lipophilic drug, wherein said drug-cochleate comprises the following components:

a) at least one drug, b) at least one negatively charged lipid component, and c) at least one divalent cation component.

Thus, the drug may be an inhibitor of viral replication such as that used in the treatment of HERPES (acyclovir), or one prescribed for it's antifungal effect on mycotic infections (miconazole nitrate). The drugs may also be those with specific targeted effects on different physiological systems such as anesthetics (propofol) which effect the nervous system, or immunosuppressants, such as cyclosporin A, which inhibit immune cell function. Other lipophilic drugs may also be selected from the groups of anti-infectious, anti-cancer, steroidal anti-inflammatory, non-steroidal anti-inflammatory, tranquilizer, or vasodilatory agents.

The instant invention further provides a cochleate formulation containing a nutrient, wherein said nutrient-cochleate comprises the following components:

a) at least one nutrient, b) at least one negatively charged lipid component, and c) at least one divalent cation component.

Specific examples include vitamin A-, polyunsaturated fatty acids- and mineral-cochleates.

The instant invention further provides a cochleate formulation containing a flavor, wherein said flavor-cochleate comprises the following components:

a) at least one essential oil or extract, b) at least one negatively charged lipid component, and c) at least one divalent cation component.

Examples include flavor substances generally associated with essential oils and extracts obtained from botanical sources such as herbs, citrus, spices and seeds. Oils/extracts are sensitive to degradation by oxidation, and because the processing of the natural oils and extracts often involves multistep operations, costs are generally considered to be higher. The advantage of an oil/extract-cochleate would be in the stabilization of these otherwise volatile and expensive flavor substances. Flavor-cochleates can also be incorporated into consumable food preparations as flavor enhancers.

The advantages of cochleates are numerous. The cochleates have a nonaqueous structure while not having an internal aqueous space, and therefore cochleates:

(a) are more stable than liposomes because the lipids in cochleates are less susceptible to oxidation;

(b) can be stored lyophilized which provides the potential to be stored for long periods of time at room temperatures, which would be advantageous for worldwide shipping and storage prior to administration;

(c) maintain structure even after lyophilization, whereas liposome structures are destroyed by lyophilization;

(d) exhibit efficient incorporation of biological molecules, particularly with hydrophobic moieties into the lipid bilayer of the cochleate structure;

(e) have the potential for slow or timed release of the biologic molecule in vivo as cochleates slowly unwind or otherwise dissociate;

(f) have a lipid bilayer matrix which serves as a carrier and is composed of simple lipids which are found in animal and plant cell membranes, so that the lipids are non-toxic, non-immunogenic and non-inflammatory;

(g) contain high concentration of divalent cation, such as, calcium, an essential mineral;

(h) are safe, the cochleates are non-living subunit formulations, and as a result the cochleates have none of the risks associated with use of live vaccines, or with vectors containing transforming sequences, such as life threatening infections in immunocompromised individuals or reversion to wild type infectivity which poses a danger to even healthy people;

(i) are produced easily and safely; and (j) can be produced as defined formulations composed of predetermined amounts and ratios of biologically relevant molecules, including polypeptides, carbohydrates and polynucleotides, such as DNA, lipophilic drugs, and nutrients such as vitamins, minerals and fatty acids.

The advantages of oral administration also are numerous. An oral route has been chosen by the WHO Children's Vaccine Initiative because of ease of administration. Oral vaccines are less expensive and much safer to administer than parenterally (intramuscular or subcutaneous) administered vaccines. The use of needles adds to the cost, and also, unfortunately, in the field, needles are often reused.

DETAILED DESCRIPTION OF THE INVENTION

Figure 1:
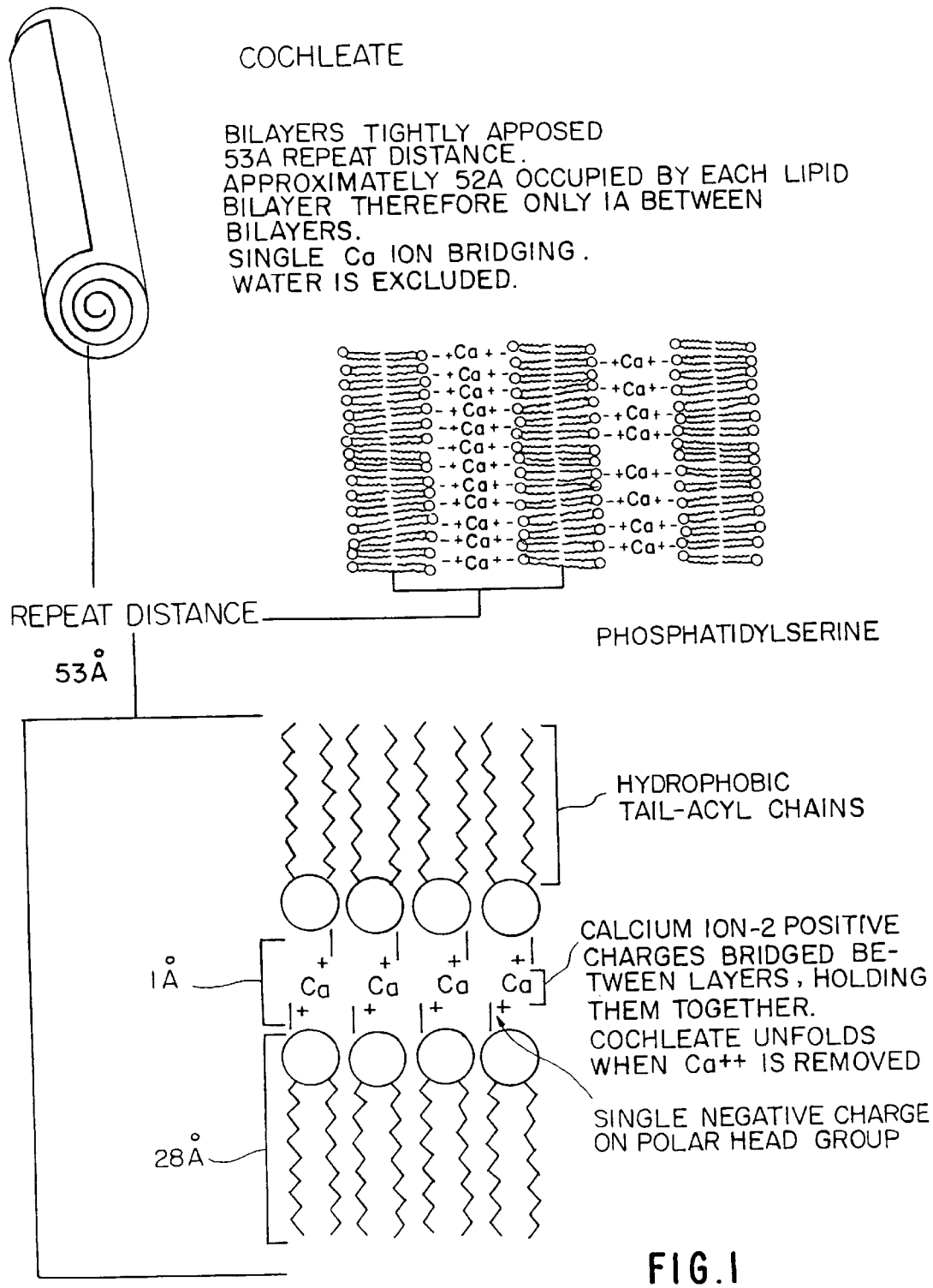
FIG. 1 is a schematic representation of a plain lipid cochleate.
Figure 2:
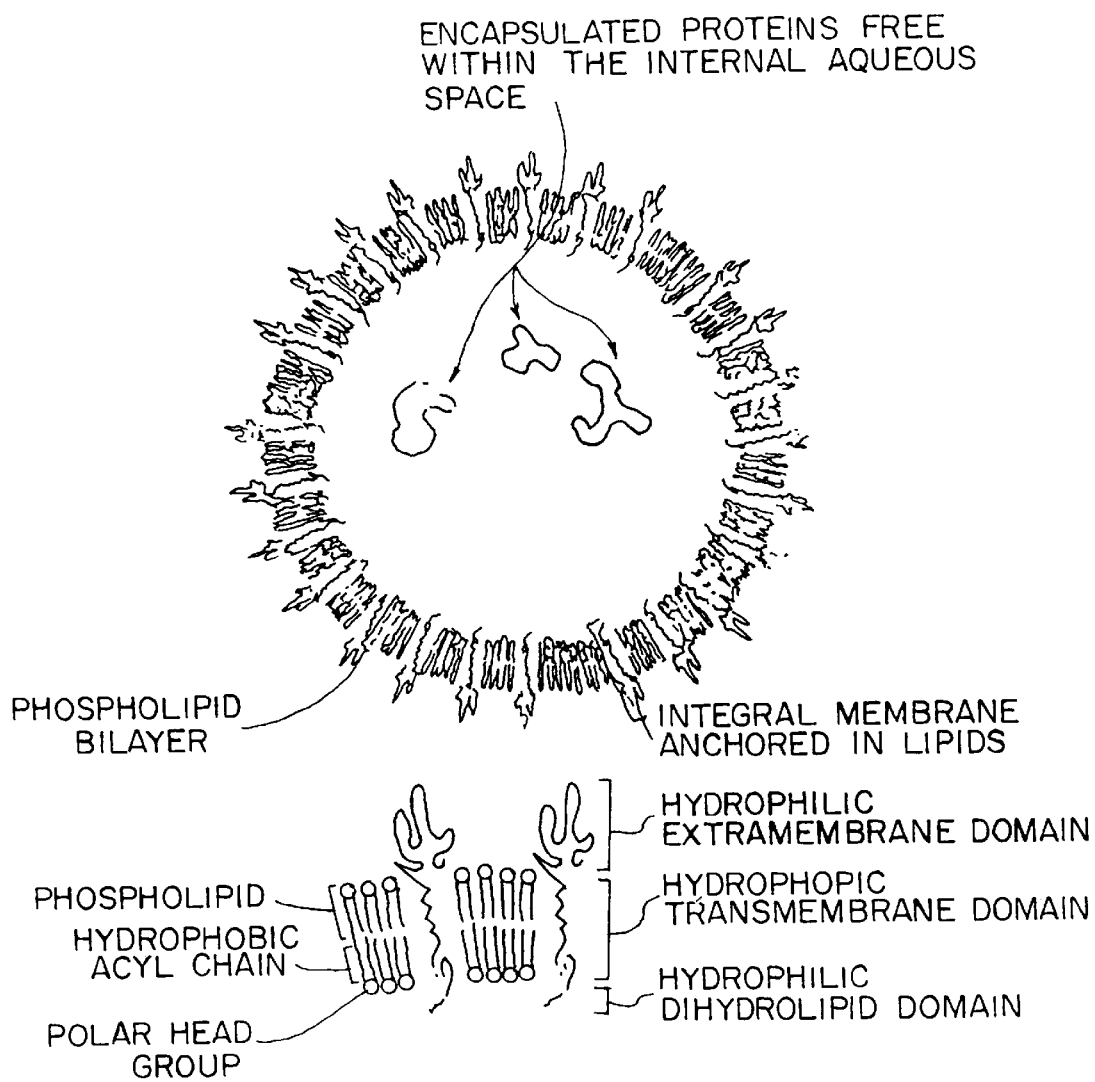
FIG. 2 shows the structure of polypeptide-lipid vesicles with integrated membrane proteins.

The instant inventors have now found surprisingly and have demonstrated that cochleates themselves be used as means for stabilizing and delivering biologic molecules. The cochleates survive the harsh acid environment of the stomach, protecting the susceptible biologic molecules immersed therein, probably by virtue of their unique multilayered precipitate structure. It is likely that cochleates then are taken up by microfold cells (M cells) in the small intestine.

The instant inventors have demonstrated that oral administration by drinking cochleates containing the glycoproteins and viral lipids from the surface of influenza or Sendai viruses plus phosphatidylserine and cholesterol, stimulate both mucosal and circulating antibody responses. In addition, strong helper cell (proliferative) and killer (cytotoxic) cell responses also are generated. Perhaps most impressively, oral administration of the influenza cochleates protects against intranasal challenge with live virus.

Those results are unexpected for a number of reasons.

It was not known and was not expected that the cochleates would survive the stomach and protect the polypeptides associated with them from the acid environment and degradative enzymes. It is known that without the presence of at least 3 mM calcium, the cochleates begin to unwind and form liposomes. It was possible, in fact likely, that the cochleates would not remain intact during the transit from the mouth, down the esophagus and through the stomach. If cochleates did come apart, they would be digested as food.

Also, having survived the stomach, that the cochleates would interact in an effective way with the mucosal and circulating immune systems was unknown and unexpected. Everyone ingests large quantities of proteins, fats and sugars on a daily basis which simply get digested and used as fuel, without stimulating any kind of mucosal or circulating immune responses. Thus, the cochleates deliver molecules which retain biologic activity at the delivery site within the host.

As used herein, the term "immune response" means either antibody, cellular, proliferative or cytotoxic activities, or secretion of cytokines.

Also, as used herein, the term "antigen" is meant to indicate the polypeptide to which an immune response is directed or an expressible polynucleotide encoding that polypeptide.

"Polynucleotide" includes DNA or RNA, as well as antisense and enzymatically active molecules. Thus the biologically relevant molecule can be the polynucleotide itself, the transcript thereof or the translated polypeptide encoded thereby.

"Polypeptide" is any oligomer or polymer of amino acids. The amino acids can be L-amino acids or D-amino acids.

A "biologically relevant molecule" is one that has a role in the life processes of a living organism. The molecule may be organic or inorganic, a monomer or a polymer, endogenous to a host organism or not, naturally occurring or synthesized in vitro and the like. Thus, examples include, vitamins, minerals, amino acids, toxins, microbicides, microbistats, co-factors, enzymes, polypeptides, polypeptide aggregates, polynucleotides, lipids, carbohydrates, nucleotides, starches, pigments, fatty acids, fatty acids of polyunsaturated form, flavored essential oils or extracts, hormones, cytokines, viruses, organelles, steroids and other multi-ring structures, saccharides, metals, metabolic poisons, drugs and the like.

The instant invention also can be practiced using whole cells other subcellular replicative entities, such as viruses and viroids. Hence, bacteria, yeasts, cell lines, viruses and the like can be mixed with the relevant lipid solution, caused to precipitate to yield structures wherein the cells and the like are fixed within the cochleate structure.

Polypeptides are suitable molecules to be incorporated with cochleates. The procedure for preparing cochleates is set forth in greater detail hereinbelow. The polypeptide is suspended in a suitable aqueous buffer. The lipids are dried to form a thin film. Then the aqueous buffer is added to the lipid film. The vessel is vortexed and then the sample dialyzed against a cation-containing buffer.

In that way, for example, cochleates carrying insulin can be obtained. The insulin cochleates were made with a 1 mg/ml solution of insulin, but various other beginning concentrations of insulin can be used to obtain cochleates loaded with varying concentrations of insulin.

Recent studies indicate that the direct injection of DNA plasmids can lead to the expression of the proteins encoded by those plasmids resulting in humoral and cell mediated immune responses, see, for example, Wang et al., *Proc. Natl Acad. Sci.* 90: 4156–4160 (1993); Zhu et al., *Science* 261: 209–211 (1993). Those studies indicate that DNA vaccines could provide a safe and effective alternative for human vaccination. Those studies also suggest that DNA vaccines could benefit from simple, more efficient delivery systems.

The use of lipids to facilitate the delivery, entry and expression of DNA in animal cells is well documented, see, for example, Philip et al., *Mol. Cell Biol.* 14: 2411–2418 (1994). Indeed, DNA-lipid complexes currently form the basis for a number of human gene therapy protocols.

Because cochleates are stable structures which can withstand a variety of physiologic conditions, cochleates are suitable means for delivering biologic molecules, such as, polypeptides or polynucleotides, to a selected site in a host. The polypeptide or polynucleotide is incorporated into and integral with the cochleate structure. Thus the polypeptide or polynucleotide, which may need to be expressed, are protected from degrading proteases and nucleases.

The cochleates used in the instant invention can be prepared by known methods such as those described in U.S. Pat. No. 4,663,161, filed Apr. 22, 1985, U.S. Pat. No. 4,871,488, filed Apr. 13, 1987, S. Gould-Fogerite et al., *Analytical Biochemistry*, Vol. 148, pages 15–25 (1985); S. Gould-Fogerite et al., *Advances in Membrane Biochemistry and Bioenergetics*, edited by Kim, C. H., Tedeschi, T., Diwan, J. J., and Salerno, J. C., Plenum Press, New York, pages 569–586 (1988); S. Gould-Fogerite et al., *Gene*, Vol. 84, pages 429–438 (1989); *Liposome Technology*, 2nd Edition, Vol. I, Liposome Preparation and Related Techniques, Vol. II, Entrapment of Drugs and Other Materials, and Vol. III, Interactions of Liposomes with the Biological Milieu, all edited by Gregory Gregoriadis (CRC Press, Boca Raton, Ann Arbor, London, Tokyo), Chapter 4, pp 69–80, Chapter 10, pp 167–184, and Chapter 17, pp. 261–276 (1993); and R. J. Mannino and S. Gould-Fogerite, Liposome Mediated Gene Transfer, *Biotechniques*, Vol. 6, No. 1 (1988), pp. 682–690.

The polynucleotide can be one which expresses a polypeptide, that is, pathogen membrane polypeptides, aberrant or atypical cell polypeptides, viral polypeptides and the like, which are known or which are suitable targets for host immune system recognition in the development of immunity thereto.

The polynucleotide may express a polypeptide which is biologically active, such as, an enzyme or structural or housekeeping protein.

Also, the polynucleotide may be one which necessarily is not expressed as a polypeptide but nevertheless exerts a biologic effect. Examples are antisense molecules and RNA's with catalytic activity. Thus, the expressed sequence may on transcription produce an RNA which is complementary to a message which, if inactivated, would negate an undesired phenotype, or produce an RNA which recognizes specific nucleic acid sequences and cleaves same at or about that site and again, the non-expression of which would negate an undesired phenotype.

The polynucleotide need not be expressed but may be used as is. Thus, the polynucleotide may be an anti.sense molecule or a ribozyme. Also, the polynucleotide may be an immunogen.

Thus, for polynucleotides, the relevant coding sequence is subcloned downstream from a suitable promoter, other regulatory sequences can be incorporated as needed, in a vector which is expanded in an appropriate host, practicing methods and using materials known and available in the art.

For example, two plasmids, pDOLHIVenv (AIDS Research and Reference Reagent Program, January 1991 catalog p. 113; Freed et al. *J. Virol.* 63: 4670 (1989)) and pCMVHIVLenv (Dr. Eric Freed, Laboratory of Molecular Immunology, NJAID, NIH) are suitable expression plasmids for use in polynucleotide-cochleates.

The plasmids contain the open reading frames for the env, tat and rev coding regions of HIV-1 (LAV strain).

pDOLHIVenv was constructed by introducing the SalI-XhoI fragment from the full length infectious molecular clone pNL4-3 into the SalI site of the retrovirus vector, pDOL (Korman et al. *Proc. Natl. Acad. Sci.* 84: 2150 (1987)). Expression is from the Moloney murine virus LTR.

pCMVHIVLenv was constructed by cloning the same SalI-XhoI fragment into the XhoI site of the cytomegalovirus (CMV)-based expression vector p763.

The polynucleotide can be configured to encode multiple epitopes or epitopes conjugated to a known immunogenic peptide to enhance immune system recognition, particularly if an epitope is only a few amino acids in size.

To form cochleate precipitates, a majority of the lipid present should be negatively charged. One type of lipid can be used or a mixture of lipids can be used. Phosphatidylserine or phosphatidylglycerol generally have been used. Phosphatidylinositol also forms a precipitate which converts to liposomes on contact with EDTA. A substantial proportion of the lipid can, however, be neutral or positively charged. The instant inventors have included up to 40 mol % cholesterol based on total lipid present and routinely make polypeptide-lipid or polynucleotide-lipid cochleates which contain 10 mol % cholesterol and 20% viral membrane lipids.

Phosphatidylethanolamine, plain or cross-linked to polypeptides, also can be incorporated into cochleates.

While negatively charged lipid can be used, a negatively charged phospholipid is preferred, and of those phosphatidylserine, phosphatidylinositol, phosphatidic acid and phosphatidylglycerol are most preferred.

One skilled in the art can determine readily how much lipid must be negatively charged by preparing a mixture with known concentrations of negative and non-negative lipids and by any of the procedures described herein, determining whether precipitates form.

Figure 3:
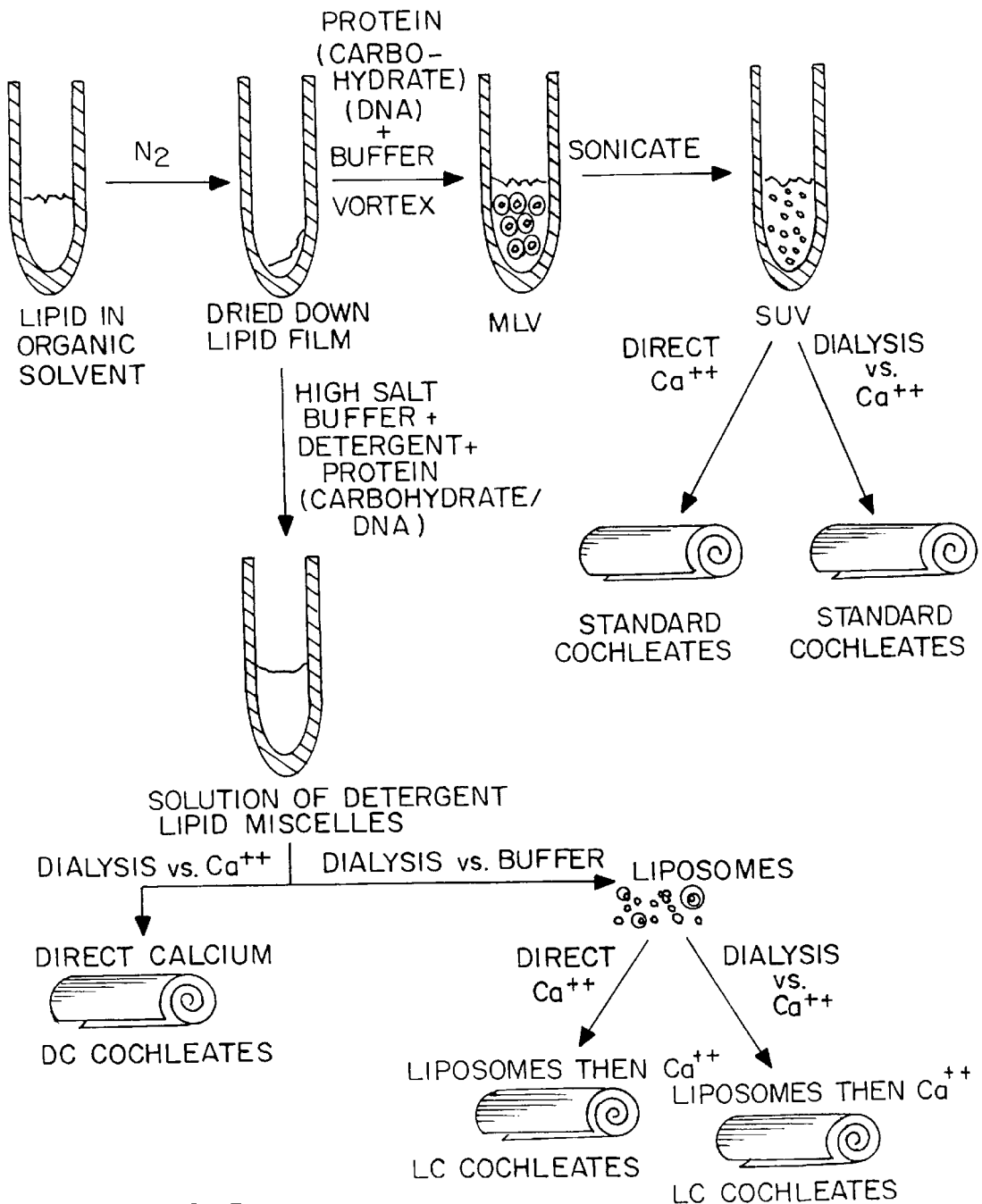
FIG. 3 summarizes the various alternative procedures for the preparation of cochleates.

There are several known procedures for making the cochleates of the instant invention and those are schematized in FIG. 3.

A suitable procedure for making cochleates is one wherein a negatively charged lipid such as phosphatidylserine, phosphatidylinositol, phosphatidic acid or phosphatidylglycerol in the absence or presence of cholesterol (up to 3:1, preferably 9:1 w/w) are utilized to produce a suspension of multilamellar lipid vesicles containing or surrounded by a biologically relevant molecule (polypeptide, polysaccharide or polynucleotide, such as DNA) which are converted to small unilamellar protein lipid vesicles by sonication under nitrogen. Alternatively, to avoid damage, the biologically relevant molecule can be added to the solution following sonication. The vesicles are dialyzed at room temperature against buffered divalent cation, e.g., calcium chloride, resulting in the formation of an insoluble precipitate which may be presented in a form referred to as a cochleate cylinder. After centrifugation, the resulting pellet can be taken up in buffer to yield the cochleate solution utilized in the instant invention.

In an alternative and preferred embodiment, an amount of negatively charged lipid, e.g., phosphatidylserine and optionally, cholesterol in the same proportions as above and equal to from about 1 to 10 times the weight, preferably equal to four times the weight of the viral or other additional lipids (including polyunsaturated fatty acids or essential oils) are utilized to prepare the cochleates. Either a polypeptide, a mineral such as calcium, magnesium, barium, iron or zinc, a vitamin such as vitamins A, D, E or K, a lipophilic drug, a flavor, a carbohydrate or polynucleotide, such as DNA, is added to the solution. That solution then is dialyzed against buffered divalent cation, e.g., calcium chloride, to produce a precipitate which can be called a DC (for direct calcium dialysis) cochleate.

An additional, related method for reconstituting cochleates has been developed and is called the LC method (liposomes before cochleates). The initial steps involving addition of extracted polypeptide, polysaccharide, polynucleotide, such as DNA or combinations thereof, to dried down negatively charged lipid and cholesterol are the same as for the DC method. However, the solution next is dialyzed against buffer (e.g., 2 mM TES, 2 mM L-histidine, 100 mM NaCl, pH 7.4) to form small liposomes containing the polypeptide, polynucleotide, such as DNA, and/or polysaccharide. A divalent cation, e.g., calcium, then is added either directly or by dialysis to form a precipitate which can consist of cochleates.

In the above procedures for making the cochleates of the instant invention, the divalent cation can be any divalent cation that can induce the formation of a cochleate or other insoluble lipid-antigen structures. Examples of suitable divalent cations include $Ca^{+2}$, $Mg^{+2}$, $Ba^{+2}$, and $Zn^{+2}$ or $Fe^{+2}$ other elements capable of forming divalent ions or other structures having multiple positive charges capable of chelating and bridging negatively charged lipids.

Cochleates made with different cations have different structures and convert to liposomes at different rates. Because of those structural differences, the rate of release of the biologically relevant molecules contained therewith varies. Accordingly, by combining cochleates made with different cations, formulations which will release the biologically relevant molecule over a protracted period of time are obtainable.

The amount of biologically relevant molecule incorporated into the cochleates can vary. Because of the advantageous properties of cochleates generally, lesser amounts of biologically relevant molecule can be used to achieve the same end result as compared to using known delivery means.

An artisan can determine without undue experimentation the optimal lipid:biologically relevant molecule ratio for the targeted purposes. Various ratios are configured and the progress of precipitation of each sample is monitored visually under a phase contrast microscope. Precipitation to form, for example, cochleates, is monitored readily Then, the precipitates can be administered to the targeted host to ascertain the nature and tenor of the biologic response to the administered cochleates.

It should be evident that the optimized ratio for any one use may range from a high ratio, for example, to minimize the use of a rare biologically relevant molecule, to a low ratio to obtain maximal amount of biologically relevant molecule in the cochleates.

Cochleates can be lyophilized and stored at room temperature indefinitely or can be stored in a divalent cation-containing buffer at 40° C. for at least six months.

The cochleate formulations also can be prepared both with and without fusogenic molecules, such as Sendai virus envelope polypeptides. Prior studies with proteoliposomes have demonstrated that cytoplasmic delivery of liposome contents requires a fusogenic liposome bilayer. The exact role of Sendai virus envelope polypeptides in facilitating the immune response to polypeptide-cochleates as yet is not clear.

It is preferred to use cochleates without fusogenic molecules over fusogenic molecule cochleates because of a more simple structure and ease of preparation favors eventual use in humans.

Because polynucleotides are hydrophilic molecules and cochleates are hydrophobic molecules that do not contain an internal aqueous space, it is surprising polynucleotides can be integrated into cochleates. The polynucleotides are not exposed on the surface of the cochleates because the polynucleotides are resistant to nucleases.

In the case of polynucleotide cochleates, considerations for dosage parallel the standard methodologies regarding vaccines as known in the art. Also, methods for using polynucleotides in liposomes and the "naked DNA" are available to serve as a baseline for empirically determining a suitable dosing regimen, practicing known methods.

For example, a suitable scheme for determining dosing is as follows.

The initial dose of polynucleotides in cochleates administered by injection to animals is selected to be about 50 μg, although it is know that as little as 2 µg of tested plasmids is effective. That dose is proposed to maximize the probability of observing a positive response following a single administration of a cochleate. Any formulations which do not elicit a response at that dose are to be considered ineffective but retained for further study.

Developing formulations which can be administered easily and non-invasively is desirable. Thus, PO administration of cochleates will be targeted and higher doses will be tried initially (100 µg/animal and 200 µg/animal). However, lower doses are required for parenteral routes.

Then graded doses will be used to develop a dose response curve for each formulation. Thus, cochleates containing 50 µg, 10 µg, 2 µg, 0.4 and 0 µg pollrnucleotide/animal will be inoculated with at least 10 animals per group.

Immune response or enzymatic activity are responses easily monitored when expression of the polynucleotide is required. Altered phenotype is another response for tracking efficacy of antisense or ribozyme type molecules. In the case of immune system monitoring, T cell proliferation, CTL and antibody presence at specific body sites can be evaluated, using known methods, to assess the state of specific immune response.

To determine the duration of activity of cochleate formulations, groups which have responded to a single immunization are monitored periodically for up to a year or more to determine the effective life of a cochleate on administration.

Animals which fail to develop a detectable response on first exposure can be re-inoculated (boosted) to provide insights into the ability of the low dose formulations to prime the immune system for later stimulation.

Pharmaceutical formulations can be of solid form including tablets, capsules, pills, bulk or unit dose powders and granules or of liquid form including solutions, fluid emulsions, fluid suspensions, semisolids and the like. In addition to the active ingredient, the formulation would comprise suitable art-recognized diluents, carriers, fillers, binders, emulsifiers, surfactants, water-soluble vehicles, buffers, solubilizers and preservatives.

An advantage of the cochleates is the stability of the composition. Thus, cochleates can be administered orally or by instillation without concern, as well as by the more traditional routes, such as topical, subcutaneous, intradermal, intramuscular and the like. Direct application to mucosal surfaces is an attractive delivery means made possible with cochleates.

The skilled artisan can determine the most efficacious and therapeutic means for effecting treatment practicing the instant invention. Reference can also be made to any of numerous authorities and references including, for example, "Goodman & Gilman's, The Pharmaceutical Basis for Therapeutics", (6th Ed., Goodman, et al., eds., MacMillan Publ. Co., New York, 1980).

The cochleates of the instant invention can be used as a means to transfect cells with an efficacy greater than using currently known delivery means, such as liposomes. Hence, the polynucleotide cochleates of the instant invention provide a superior delivery means for the various avenue of gene therapy, Mulligan, *Science* 260: 926–931 (1993). As Mulligan noted, the many possibilities of treating disease by gene-based methods will be enhanced by improved methods of gene delivery.

The cochleates of the instant invention also serve as excellent means for delivering other biologically relevant molecules to a host. Such biologically relevant molecules include nutrients, vitamins such as vitamins A, D, E or K, co-factors, enzymes, fatty acids such as polyunsaturated forms, minerals including divalent cations such as calcium, magnesium, zinc, iron or barium, flavors and the like. Because the biologically relevant molecule is contained within the cochleate, in a non-aqueous environment, the biologically relevant molecule essentially is stabilized and preserved. As described hereinabove, the biologically relevant molecule is added to the lipid solution and processed to form a precipitated structure comprising lipid and biologically relevant molecule. As demonstrated herein, hydrophilic molecules can be "cochleated", that is, can be made part of the cochleate structure, with little difficulty.

Also, suitable lipophilic biologically relevant molecules, such as drugs and other therapeutic compounds, are amenable to cochleation. For example, lipophilic drugs such as cyclosporin, ivermectin and amphotericin are readily cochleated. Other lipophilic drugs which are amenable to incorporation into cochleates are acyclovir, propanidid, propofol, alphadione, echinomycine, miconazole nitrate, teniposide, didemnin B, hexamethylmelamine, taxol, taxotere, melphalan, adriamycin, 18-hydroxydeoxycorticosterone, rapamycine, prednisolone, dexamethazone, cortisone, hydrocortisone, pyroxicam, naproxen, diazepam, verapamil, nifedipine.

The instant invention now will be described by means of specific examples which are not meant to limit the invention.

EXAMPLE 1

Bovine brain phosphatidylserine in chloroform was purchased from Avanti Polar Lipids, Birmingham, Alabama in glass ampules and stored under nitrogen at −20° C. Cholesterol (porcine liver) grade I, α-D-octyl-glucopyranoside (OCG), fluorescein isothiocyanate (FITC)-dextran (average mol. wt. 67,000), metrizamide grade I, and chemicals for buffers and protein and phosphate determinations, were obtained from Sigma Chemical Company, St. Louis, Mo. organic solvents were purchased from Fisher Scientific Co., Fairlawn, N.J. Reagents for polyacrylamide gel electrophoresis were from BioRad Laboratories, Richmond, Calif. S1000 Sephacryl Superfine was obtained from Pharmacia, Piscataway, N.J. Thick walled polycarbonate centrifuge tubes (10 ml capacity) from Beckman Instruments, Palo Alto, Calif., were used for vesicle preparations, washes, and gradients. A bath type sonicator, Model G112SP1G, from Laboratory Supplies Company, Hicksville, N.Y. was used for sonications.

Virus was grown and purified essentially as described by M. C. Hsu et al., *Virology*, Vol. 95, page 476 (1979). Sendai (parainfluenza type I) and influenza (A/PR8/34) viruses were propagated in the allantoic sac of 10 or 11 day old embryonated chicken eggs. Eggs were inoculated with 1–100 egg infectious doses ($10^3$ to $10^5$ viral particles as determined by HA titer) in 0.1 ml of phosphate buffered saline (0.2 gm/L KCl, 0.2 gm/L $KH_2PO_4$, 8.0 gm/L NaCl, 1.14 gm/L $Na_2H-PO_4$, 0.1 gm/L $CaCl_2$, 0.1 gm/L $MgCl_2 6H_2O$ (pH 7.2)). Eggs were incubated at 37° C. for 48 to 72 hours, followed by incubation at 4° C. for 24 to 48 hours. Allantoic fluid was collected and clarified at 2,000 rpm for 20 minutes at 5° C. in a Damon IEC/PR-J centrifuge. The supernatant was then centrifuged at 13,000 rpm for 60 minutes. This and all subsequent centrifugations were performed in a Sorvall RC2-B centrifuge at 5° C. using a GG rotor. The pellets were resuspended in phosphate buffered saline (pH 7.2) by vortexing and sonicating, followed by centrifugation at 5,000 rpm for 20 minutes. The pellet was resuspended by vortexing and sonicating, diluting, and centrifuging again at 5,000 rpm for 20 minutes. The two 5,000 rpm supernatants were combined and centrifuged at 13,000 rpm for 60 minutes. The resulting pellets were resuspended in phosphate-buffered saline by vortexing and sonicating, aliquoted, and stored at $-70°$ C. Sterile technique and materials were used throughout viral inoculation, isolation, and purification.

Virus stored at $-70°$ C. was thawed, transferred to sterile thick-walled polycarbonate tubes and diluted with buffer A (2 mM TES, 2 mM L-histidine, 100 mM NaCl (pH 7.4)). Virus was pelleted at 30,000 rpm for 1 hour at $5°$ C. in a Beckman TY65 rotor. The supernatant was removed and the pellet resuspended to a concentration of 2 mg viral protein per ml of extraction buffer (EB) (2 M NaCl, 0.02 M sodium phosphate buffer (pH 7.4)) by vortexing and sonicating. The nonionic detergent $\alpha$-D-octyl-glucopyranoside was then added to a concentration of 2% (w/v). The suspension was mixed, sonicated for 5 seconds and placed in a $37°$ C. water bath for 45 minutes. At 15, 30 and 45 minute incubation times, the suspension was removed briefly for mixing and sonication. Nucleocapsids were pelleted by centrifugation at 30,000 rpm for 45 minutes in a TY65 rotor. The resulting clear supernatant was removed and used in the formation of viral glycoprotein-containing cochleates. Some modification of the above procedure may have to be employed with other membrane proteins. Such modifications are well known to those skilled in the art.

EXAMPLE 2

A. DC Cochleates.

An amount of phosphatidylserine and cholesterol (9:1 wt ratio) in extraction buffer and non-ionic detergent as described hereinabove was mixed with a pre-selected concentration of polynucleotide and the solution was vortexed for 5 minutes. The clear, colorless solution which resulted was dialyzed at room temperature against three changes (minimum 4 hours per change) of buffer A (2 mM TES N-Tris[hydroxymethyl]-methyl-2 aminoethane sulfonic acid, 2 mM L-histidine, 100 mM NaCl, pH 7.4, also identified as TES buffer) containing 3 mM $CaCl_2$. The final dialysis routinely used is 6 mM $Ca^{2+}$, although 3 mM $Ca^{2+}$ is sufficient and other concentrations may be compatible with cochleate formation. The ratio of dialyzate to buffer for each change was a minimum of 1:100. The resulting white calcium-phospholipid precipitates have been termed DC cochleates. When examined by light microscopy (x 1000, phase contrast, oil), the suspension contains numerous particulate structures up to several microns in diameter, as well as needle-like structures.

B. LC Cochleates.

An amount of phosphatidylserine and cholesterol (9:1 wt ratio) in extraction buffer and non-ionic detergent as described hereinabove was mixed with a pre-selected concentration of polynucleotide and the solution was vortexed for 5 minutes. The solution first was dialyzed overnight using a maximum ratio of 1:200 (v/v) of dialysate to buffer A without divalent cations, followed by three additional changes of buffer leading to the formation of small protein lipid vesicles. The vesicles were converted to a cochleate precipitate, either by the direct addition of $Ca^{2+}$ ions, or by dialysis against two changes of buffer A containing 3 mM $Ca^{2+}$ ions, followed by one containing buffer A with 6 mM $Ca^{2+}$.

EXAMPLE 3

IMMUNE RESPONSES TO ORALLY DELIVERED PROTEIN-COCHLEATE VACCINES

To make the vaccine, influenza virus was grown, purified, and the glycoproteins and lipids extracted and isolated as described in Example 1. Protein-cochleates were made according to the "LC cochleate" procedure described above.

Figure 4A:
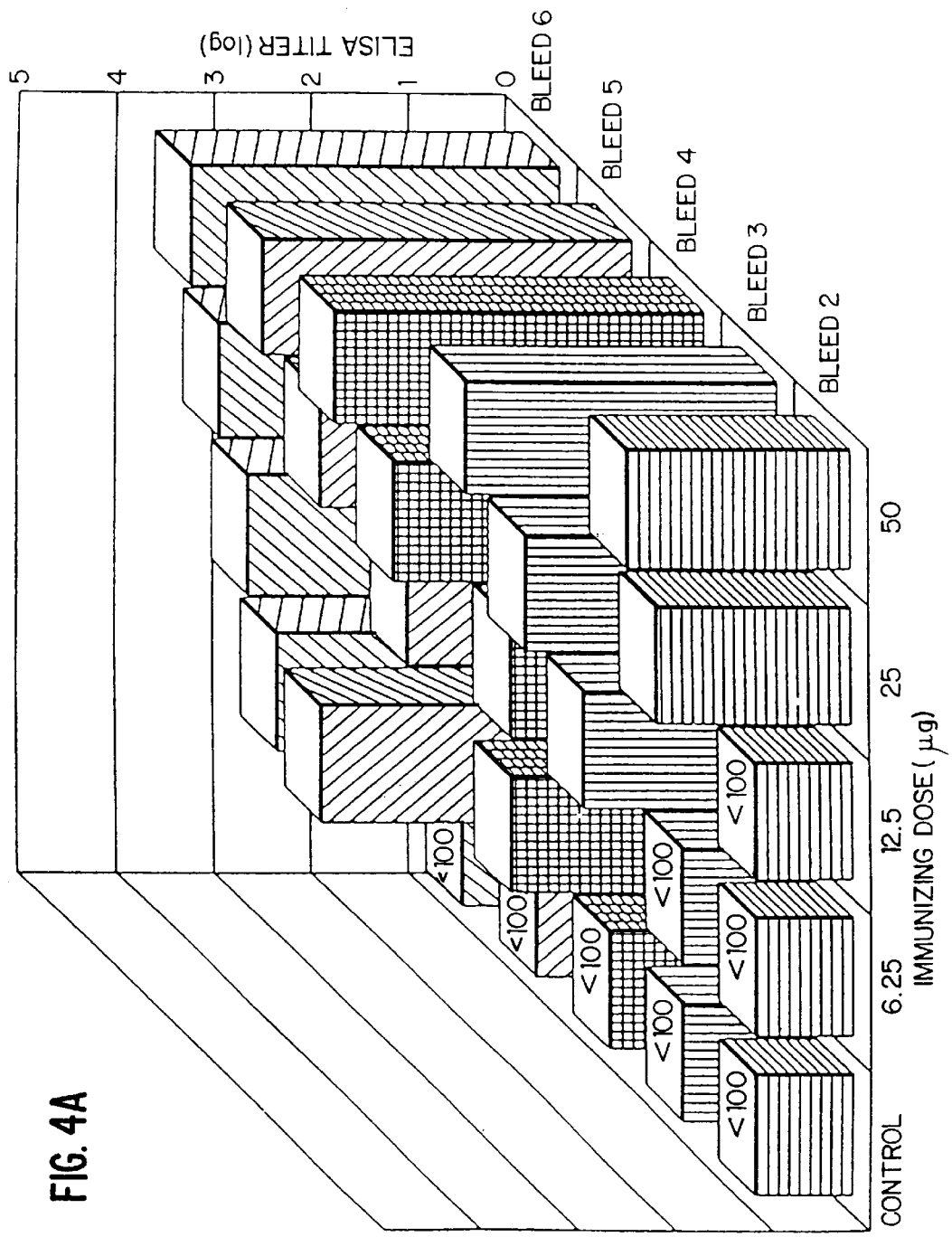
FIGS. 4(A) and 4(B) show serum antibody titers in mice following oral administration of influenza polypeptide-cochleates.

Cochleate vaccines containing the glycoproteins and lipids from the envelope of influenza virus and phosphatidylserine and cholesterol were given to mice by gradually dispensing 0.1 ml liquid into the mouth and allowing it to be comfortably swallowed. FIGS. 4(A) (from Experiment A) and 4(B) (from Experiment B) show resulting total circulating antibody levels specific for influenza glycoproteins, as determined by ELISA. Antibody titer is defined as the highest dilution that still gives the optimal density of the negative control.

In Experiment A that generated the data shown in FIG. 4(A), initial vaccine doses of 50, 25, 12.5 or 6.25 $\mu$g of glycoproteins (groups 1 through 4 respectively) were administered at 0 and 3 weeks. The third and fourth immunizations (6 and 19 weeks) were at one fourth the dose used for the initial two immunizations. Bleed 1–Bleed 6 occurred at 0, 3, 6, 9, 19, and 21 weeks. The data demonstrate that high circulating antibody titers can be achieved by simply drinking cochleate vaccines containing viral glycoproteins. The response is boostable, increasing with repeated administration, and is directly related to the amount of glycoprotein in the vaccine.

Figure 4B:
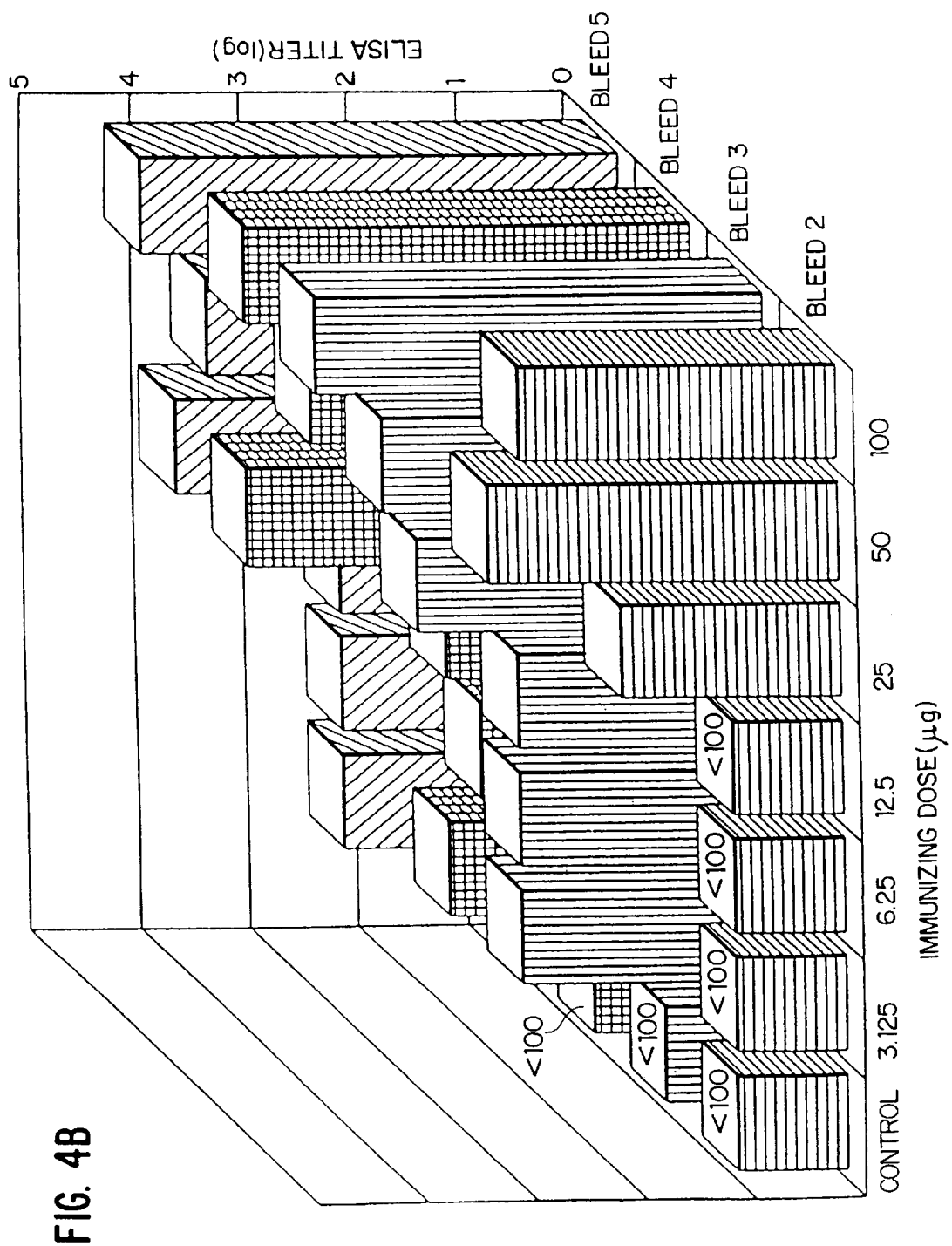

Those observations were confirmed and extended in Experiment B that generated the data shown in FIG. 4(B). The dose range was expanded to include 100 $\mu$g and 3.1 $\mu$g initial doses. Vaccine was given at 0, 3 and 15 weeks, with the third immunization at one fourth the dose of the initial two. Bleed 1 to Bleed 6 occurred at 0, 3, 6, 15 and 16 weeks. Circulating influenza glycoprotein-specific responses were detectable after a single administration for the top five doses, and for all groups after two feedings. The data shown is for pooled sera from each group, but all mice given the four highest doses, and four of five mice in groups five and six, responded to the vaccine with circulating antibody titers ranging from 100 to 102,400. Group seven, which received no vaccine, had titers less than 50 for all mice at all time points.

The antibody response is long lived. Titers 13 weeks after the third immunization (FIG. 4(A), bleed 5) and 12 weeks after the second immunization (FIG. 4(B), bleed 4) remained the same or within one dilution higher or lower than seen at 3 weeks after the previous boost.

To determine whether oral administration of the subunit vaccine described in Example 2 could lead to protective immunity in the respiratory tract, the mice described in Experiment B of Example 2 were immunized with cochleates at 0, 3 and 15 weeks. The immunized mice were challenged by intranasal application of $2.5 \times 10^9$ particles of influenza virus at 16 weeks. Three days after viral challenge, mice were sacrificed, and lungs and trachea were obtained. The entire lung or trachea was triturated and sonicated, and aliquots were injected into embryonated chicken eggs to allow amplification of any virus present. After three days at $37°$ C., allantoic fluid was obtained from individual eggs and hemagglutination (HA) titers were performed.

Mice were also challenged with live influenza intranasally following oral cochleate administration in Experiment A of Example 2. Lungs were obtained three days later and cultured to detect presence of virus.

Figure 5:
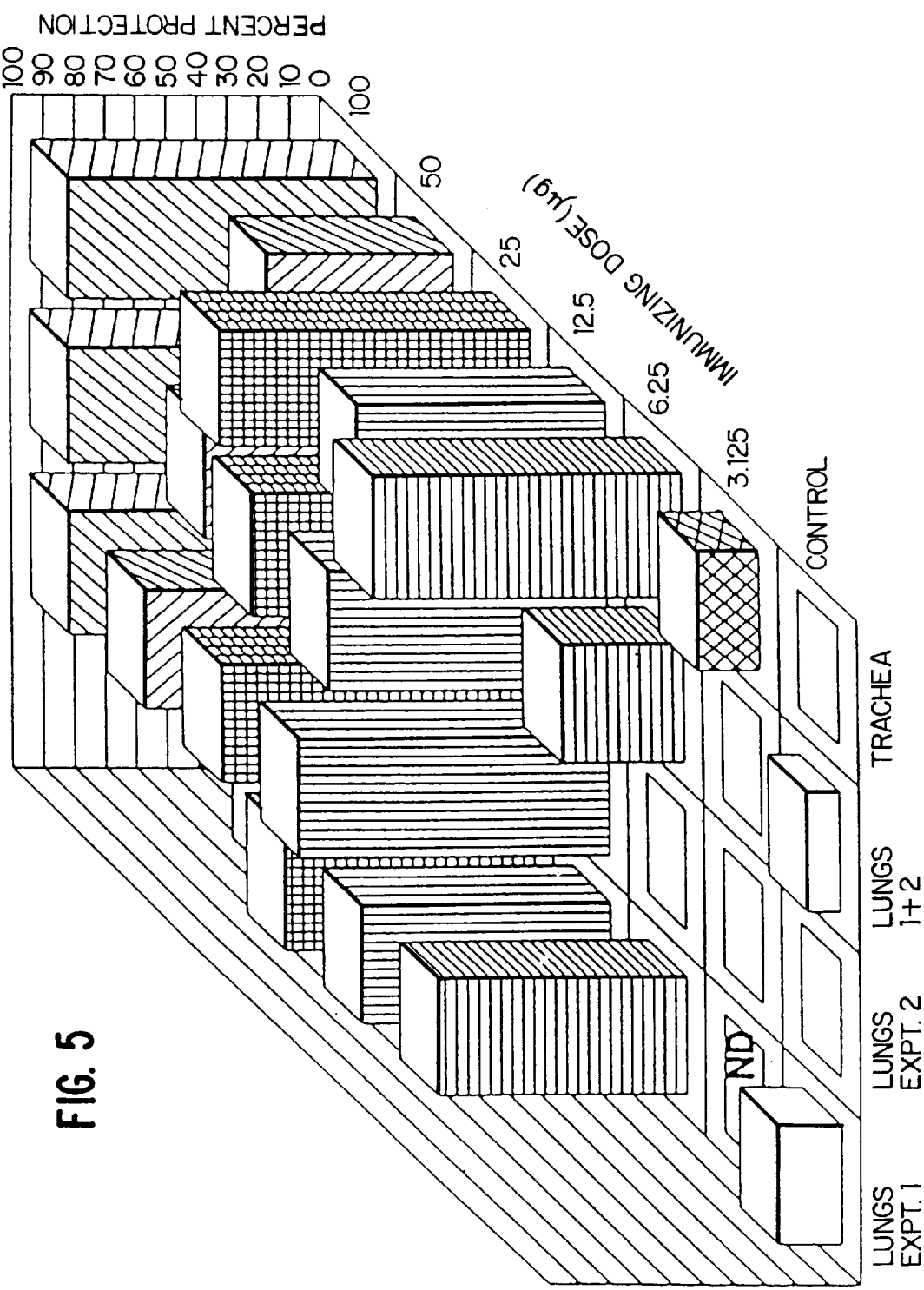
FIG. 5 is a graph showing the results of oral administration of polypeptide-cochleates when challenged with live virus.

The combined data for the two experiments is given in Table 1. The results also are shown graphically in FIG. 5.

TABLE 1

| Vaccine Dose µg Protein | Trachea[1] # Infected/ Total | Lungs[2] # Infected/ Total | Lungs[3] # Infected/ Total |
| --- | --- | --- | --- |
| 100 | 0/5 | 0/5 | 0/5 |
| 50 | 2/5 | 0/5 | 2/10 |
| 25 | 0/5 | 0/5 | 1/10 |
| 12.5 | 1/5 | 0/5 | 1/10 |
| 6.25 | 0/5 | 5/5 | 6/10 |
| 3.12 | 4/5 | 5/5 | 5/5 |
| 0 | 5/5 | 5/5 | 9/10 |

[1]Mice from Experiment B.
[2]Mice from Experiment B.
[3]Mice from Experiments A and B.

The data in Table 1 shows that all five of the unvaccinated mice had sufficient virus in the trachea to infect the embryonated chicken eggs (greater than $10^3$ particles per trachea or at least one egg infectious dose (EID) per 0.1 ml of suspension). In contrast, the oral vaccine provided a high degree of protection from viral replication in the trachea. All mice in groups 1, 3 and 5 of Experiment B were negative for virus. Two mice in group 2, 1 in group 4, and 4 in group 6 (the lowest vaccine dose) of Experiment B had sufficient virus to test positive in this very sensitive assay used to detect presence of virus.

The oral protein cochleate vaccine also provided protection against viral replication in the lungs. All twenty mice which received the four highest doses of vaccine were negative for virus when lung suspensions were cultured in embryonated chicken eggs (Table 1). All mice in the groups immunized with 6.25 µg and 3.1 µg glycoproteins and all mice in the unvaccinated control were positive for virus.

Even in the lowest two vaccine doses, there was some inhibition of viral replication. When lung suspensions were diluted 1/10 and inoculated into eggs, only one animal in the groups immunized with 6.25 µg was positive, as compared to three in the groups immunized with 3.12 µg and three in the unvaccinated control. Culturing of 1/100 dilutions resulted in one positive animal in each of the groups immunized with 6.25 and 3.12 µg, but 3 of 5 remained positive in the unvaccinated group. In addition, for the two animals in the group that was immunized with 3.12 µg, but which were negative at 1/100, only 50% of the eggs were infected at 1/10 and had low HA titers. In contrast, for the unvaccinated group, all eggs were infected and produced maximal amounts of virus at 1/10 and 1/100 dilutions.

Figure 6:
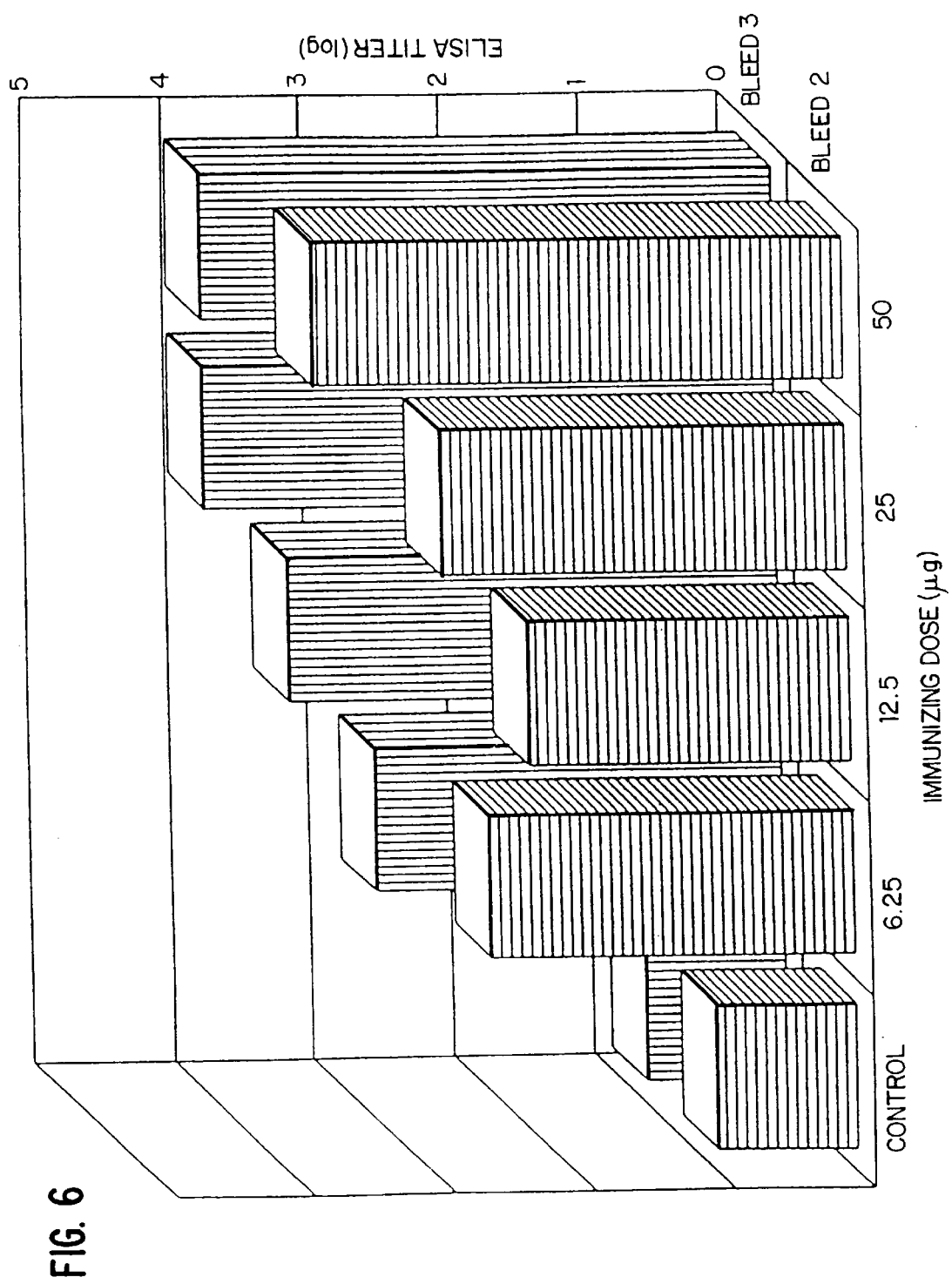
FIG. 6 is a graphic representation of serum antibody titers in mice following oral administration of Sendai-cochleates.

C57BL/6 mice were given cochleates containing Sendai virus glycoproteins orally at 0 and 3 weeks. They were bled at 0 (bleed 1), 3 (bleed 2), and 6 (bleed 3) weeks. Group 1 received approximately 50 µg protein, Group 2 about 25 µg, Group 3 about 12.5 µg, Group 4 about 6.25 µg, and Group 5 (negative control) received 0 µg protein. The levels of Sendai specific antibodies in the serum pooled from 5 mice in each dose group were determined by ELISA. The results are shown in FIG. 6. It can be seen that strong antibody responses were generated, that the magnitude of the response was directly related to the immunizing dose, and that the magnitude of the response increased (boosted) after a second immunization.

The response was extremely long-lived. The response is predominantly IgG, indicative of the involvement in T cell help and establishment of long-term memory cells associated with a secondary immune response. Surprisingly, the lowest dose which initially had the lowest response, now had the highest circulating antibody levels. This may be due to the immune system's down regulation of the very high responses originally but allowing the low response to slowly climb. This may also indicate a persistence and slow release of antigen. It is also interesting and consistent with the use of the oral route of immunization that significant IgA titers are generated and maintained.

Figure 7:
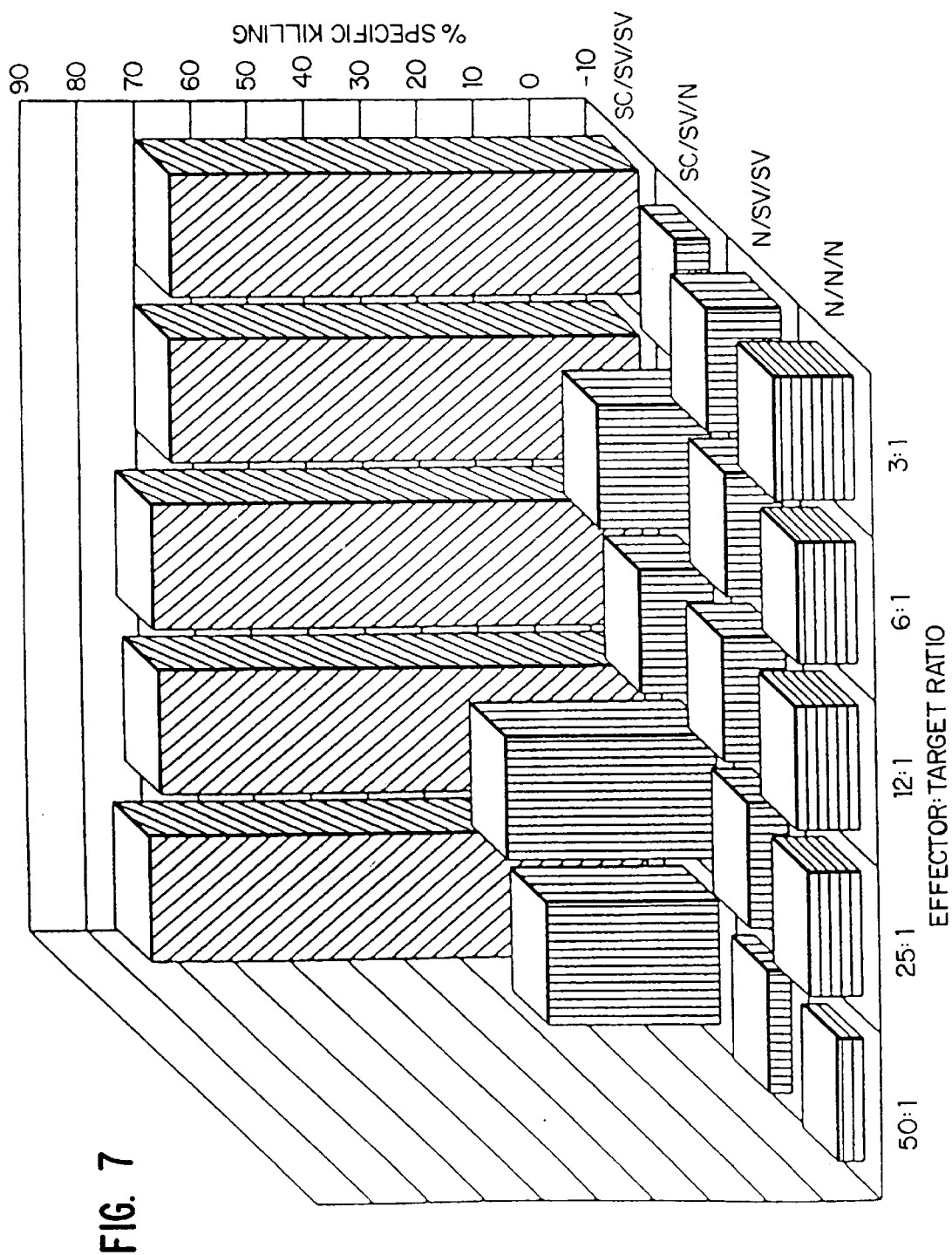
FIG. 7 is a graph depicting the induction of antigen-specific cytotoxic splenocytes following oral administration of Sendai cochleates.

A 50 µg protein dose of Sendai glycoprotein-containing cochleates was given orally. Two weeks later the animal (BALB/c mouse) was sacrificed and spleen cells obtained. Cytolytic activity of the spleen cells was measured by their ability to cause the release of chromium-51 from target cells presenting Sendai antigens. The non-immunized mouse did not kill Sendai virus (SV) pulsed cells with in culture restimulation (N/SV/SV) or non-Sendai presenting cells (N/N/N). (FIG. 7) In contrast, Sendai cochleate immunized mice killed SV pulsed targets to a very high degree and non-pulsed targets to a lesser degree. Cytolytic activity is crucial to clearance of cells infected viruses, or intracellular parasites or to cancer cells. It is a highly desirable activity for a vaccine to induce, but classically has not been seen with most non-living vaccines. This is an important feature of protein-cochleate vaccines.

EXAMPLE 4

Eight week old BALB/c female mice were immunized IM twice with various polynucleotide-cochleate formulations, polynucleotide alone and controls and then splenocytes from the mice were tested for the ability to proliferate in response to a protein encoded by the polynucleotide.

Cochleates with and without fusogenic Sendai virus protein were prepared as described hereinabove. The polynucleotide used was the pCMVHIVLenv plasmid. The solution containing lipid and extracted Sendai virus envelop proteins as described hereinabove and polynucleotide were mixed at a 10:1 (w/w) ratio and 50:1 (w/w) ratio. That protocol yielded four groups, cochleate/DNA, 10:1; cochleate/DNA, 50:1; SV-cochleate/DNA, 10:1; and SV-cochleate/DNA, 50:1. Naked DNA was used at a rate of 10 µg/mouse and 50 µg/mouse. The control was buffer alone. Mice were immunized twice, 15 days apart at 50 µl/mouse.

Splenocytes were obtained and tested in a T-cell proliferation assay using tritiated thymidine, as known in the art. Control cultures contained no antigen or con A. The antigen used was p18 peptide, at 1 mM, 3 mM and 6 mM. Cells were harvested at days 2, 4 and 6 following preparation of the splenocyte cultures.

The naked DNA provided a marginal response above background. All four cochleate preparations yielded a p18-specific response which increased over time. At six days, the response was about four times above background.

The DNA concentration range at the 10:1 ratio was about 120–170 µg/ml. At the 50:1 (w/w) ratio; the DNA concentration was about 25–35 µg/ml.

The polynucleotide-cochleates were exposed to micrococcal nuclease and little or no nucleic acid degradation was observed.

The polynucleotide encapsulation efficiency was found to be about 50% based on quantification of free DNA from lipid, that is present in the supernatant following a precipitation reaction. After washing the precipitate and opening the structures by removing cation about 35% of the DNA was recovered.

EXAMPLE 5

In similar fashion, splenocytes from animals immunized as described in Example 4, were tested for antigen specific cytotoxic activity using a chromium release assay using labelled H-2 compatible target cells known to express an HIV protein, such as gp160. The responder cells can be stimulated by brief exposure to purified HIV peptides.

On prestimulation, animals exposed to polynucleotide cochleates demonstrated specific cytotoxic splenocytes directed to gp160, with nearly 100% cytotoxicity observed at an effector:target ratio of 100.

EXAMPLE 6

Fifteen mg of insulin were added to 15 ml of extraction buffer (EB) in a 50 ml plastic tube. Then 300 mg of OCG were added to the mixture. The resulting suspension was colloidal and not clear at pH 7.4. The solution was titrated with 1 N NaOH to pH 8.5, resulting in a clear solution.

In a separate vessel, 6.8 ml of a 10 mg/ml solution of phosphatidylserine and 1.5 ml of a 5 mg/ml solution of cholesterol were mixed and then dried to yield a thin film. The insulin solution was added to the vessel yielding a colloidal suspension. The suspension was vortexed for seven minutes and then set on ice for one hour. The pH of the solution was adjusted to 9–9.5 with 1 N NaOH, the sample was filter sterilized and placed in dialysis tubing at about 2 ml per bag.

Two different dialysis schedules were used.
A. DC cochleates:
1. 100 ml overnight 1×TES pH 9.0 containing 3 mM $Ca^{+2}$, $Zn^{+2}$ or $Mg^{+2}$
2. 250 ml 4h 1×TES pH 8.5 containing 3 mM $Ca^{+2}$, $Zn^{+2}$ or $Mg^{+2}$
3. 250 ml 4 h 1×TES pH 8.0 containing 3 mM $Ca^{+2}$, $Zn^{+2}$ or $Mg^{+2}$
4. 250 ml 4 h 1×TES pH 7.4 containing 6 mM $Ca^{+2}$, $Zn^{+2}$ or $Mg^{+2}$
B. LC cochleates:
1. 100 ml overnight 1×TES, pH 9.0
2. 250 ml 4 h, 1×TES, pH 9.0
3. 250 ml 4 h 1×TES, pH 9.0
4. 100 ml overnight 1×TES, pH 9.0 containing 3 mM $Ca^{+2}$, $Zn^{+2}$ or $Mg^{+2}$
5. 250 ml 4 h 1×TES, pH 8.5 containing 3 mM $Ca^{+2}$, $Zn^{+2}$ or $Mg^{+2}$
6. 250 ml 4 h 1×TES, pH 7.4 containing 6 mM $Ca^{+2}$, $Zn^{+2}$ or $Mg^{+2}$ Following dialysis, the resulting precipitate was found to comprise numerous cochleates.

EXAMPLE 7

Mice were given insulin cochleate samples orally. Serum glucose levels were measured at 0 time, (prior to cochleate administration), 30 min. and 60 min. post administration using standard methods. Cochleate formulations of Example 6 with a starting concentration of 1 mg insulin/ml solution were used. Each mouse was administered 100 ul or 200 ul of the designated preparations as indicated. For comparison, one mouse was given the standard commercial human insulin, Humulin R, by intraperitoneal administration.

| Sample | Volume Given | Serum Glucose mg/dl | | |
|---|---|---|---|---|
| | | 0 Time | 30 min. | 60 min. |
| LC Ca++ | 200 ul | 100 | 49.12 | 43 |
| LC Ca++ | 200 ul | 102.9 | 252.4 | 61.9 |
| Humulin R | 200 ul | 88.8 | 66 | 48.5 |

Oral administration of insulin affected serum glucose levels.

EXAMPLE 8

Insulin cochleates as produced in Example 6 were fed orally to three-month-old female BALB/c mice made diabetic through intraperitoneal injection of streptozotocin, practicing known methods. Two days after exposure to streptozotocin, the mice were allocated into groups of five and administered with oral insulin cochleates at 200 μl per mouse. Other mice were injected with 2 IU of Humulin R.

Figure 8:
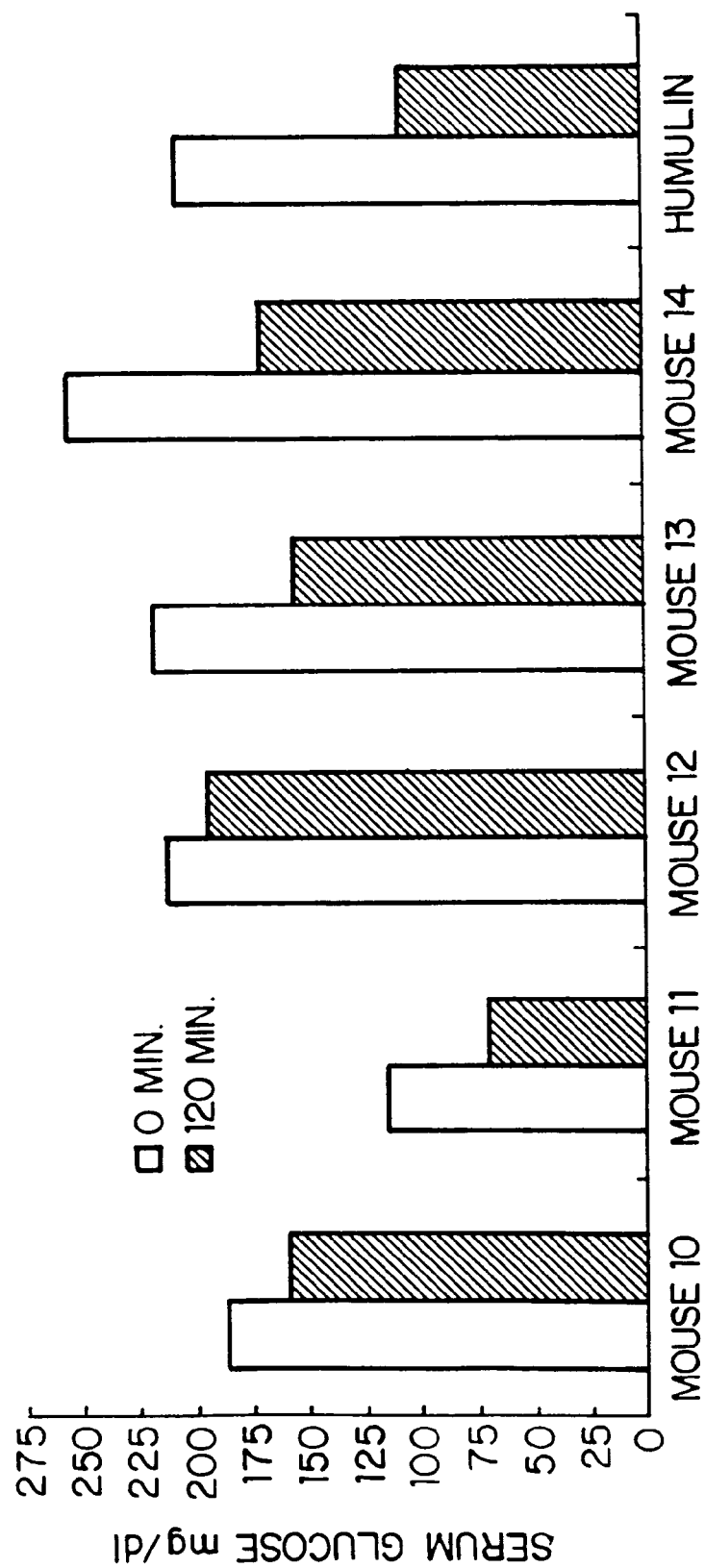
FIG. 8 provides a series of bar graphs depicting serum glucose levels before and after oral insulin administration.

Serum samples were obtained at time 0, prior to insulin dosing, and two hours post insulin administration. Glucose levels were measured using a kit from Sigma (St. Louis). Control animals were untreated, that is, received no streptozotocin or insulin. Representative data are set forth in FIG. 8. Orally administered insulin, simply by drinking, was effective in reducing blood glucose levels. No reduction in blood glucose was observed in control animals.

All references cited herein are incorporated by reference in entirety.

While the invention has been described in detail and with reference to specific embodiments thereof, it will be apparent to one skilled in the art that various changes and modifications can be made therein without departing from the spirit and scope thereof.

NUTRIENT-COCHLEATES

EXAMPLE 8

Vitamin A in Cochleates

Vitamin A (retinol) is sensitive to air-oxidation and is inactivated by ultraviolet light. Stability of vitamin A is enhanced by its encapsulation into the intra-bilayers of cochleates. Incorporation of vitamin A into the intra-bilayer phospholipid region of a cochleate was achieved as follows: appropriate proportions of vitamin A, phosphatidylserine and cholesterol were dissolved in an organic solvent such as chloroform or a 1:1 methanol:chloroform mixture. The solvent was then removed under reduced pressure to yield a lipid-vitamin film. Buffer was added and the mixture was vortexed for several minutes. The resultant dispersion was then dialyzed at room temperature as in example 2. A against three changes of buffer A containing 3 mM $CaCl_2$. Vitamin A-cochleates were obtained as a precipitate.

EXAMPLE 9

Polyunsaturated Fatty Acids in Cochleates

Unsaturated fatty acids are biologically important in that they control the level of cholesterol in blood and are the precursors of prostaglandins. The limitation in incorporating polyunsaturated fats in food is their susceptibility to oxidation. In the presence of oxygen, unsaturated fatty acids undergo a series of reactions called autoxidation, whose final products are aldehydes and ketones, which provide fishy unpleasant odor and flavor. An interesting way to control autoxidation of unsaturated fats is to incorporate them into the bilayers of a cochleate. The polyunsaturated fatty acids (PUFA) are placed in close contact with oxygen-stable saturated fatty esters of the phosphatide. Incorporation, for example, of fish oils (which are rich in PUFA) into the intra-bilayer phospholipid region of a cochleate is achieved as follows: appropriate proportions of fish oil, phosphatidy:Lserine and cholesterol (or optionally alpha-tocopherol as a stabilzer and autoxidant), are dissolved in organic solvent such as chloroform or a 1:1 methanol:chloroform mixture. The solvent is then removed under reduced pressure to yield a lipid film. Buffer is added and the mixture is vortexed for several minutes. The resultant dispersion is then dialyzed at room temperature as in example 2. A against three changes of buffer A containing 3 mM CaCl$_2$. PUFA-cochleates are obtained as a precipitate.

EXAMPLE 10

Cinnamon Oil in Cochleates

Flavors are volatile and sensitive to oxidation. Controlled release and enhanced physical and chemical stability is achieved by the encapsulation of flavors into cochleates. Incorporation of a flavor based on cinnamon oil into the intra-bilayer phospholipid region of a cochleate is achieved as follows: phosphatidylserine and cholesterol are dissolved in an organic solvent such as chloroform or a 1:1 methanol:chloroform mixture, and an appropriate proportion of cinnamon oil dissolved in ethanol is added. The solvent is then removed under reduced pressure to yield a film. Buffer is added and the mixture is vortexed for several minutes. The resultant dispersion was then dialyzed at room temperature as in example 2. A against three changes of buffer 1A containing 3 mM CaCl$_2$. Cinnamon oil-cochleates are obtained as a precipitate.

LIPOPHILIC DRUG COCHLEATES

EXAMPLE 11

Acyclovir in Cochleates

Incorporation of acyclovir into the intrabilayer phospholipid region of a cochleate is achieved as follows: acyclovir/phosphatidylserine in an appropriate drug to lipid ratio is dissolved in an organic solvent such as chloroform or a 1:1 methanol:chloroform mixture. The solvent is then removed under reduced pressure to yield a homogenous film. Buffer is added and the mixture is vortexed for several minutes at a temperature above the transition temperature of the lipid. The excess drug, if any, is separated from the liposome containing acyclovir by repeated washing with PBS and centrifugation, the supernatant is discarded, and the pellet resuspended in PBS. The liposome suspension is then dialyzed at room temperature as in example 2. A against three changes of buffer A containing 3 mM CaCl$_2$. Acyclovir-cochleates are obtained as a precipitate.

EXAMPLE 12

Hydrocortisone in Cochleates

Incorporation of hydrocortisone into the intra-bilayer phospholipid region of a cochleate is achieved as follows: hydrocortisone/phosphatidylserine in an appropriate drug to lipid ratio are dissolved in an organic solvent such as chloroform or a 2:1 methanol:chloroform mixture. The solvent is then removed under reduced pressure to yield a homogeneous film. Buffer is added and the mixture is vortexed for several minutes at a temperature above the transition temperature of the lipid. The excess drug, if any, is separated from the liposome containing hydrocortisone by repeated washing with PBS and centrifugation, the supernatant is discarded, and the pellet resuspended in PBS. The liposome suspension is then dialyzed at room temperature as in example 2. A against three changes of buffer A containing 3 mM CaCl$_2$. Hydrocortisone-cochleates are obtained as a precipitate.

What is claimed is:

1. A nutrient-cochleate formulation comprising:
   a) a nutrient component and
   b) a cochleate further comprising a negatively charged lipid component and a divalent cation component.
2. The nutrient-cochleate formulation of claim 1, wherein said nutrient is of a mineral, an amino acid, a vitamin, a lipid, a fatty acid, or a saccharide.
3. The nutrient-cochleate formulation of claim 1, wherein the nutrient is a mineral.
4. The nutrient-cochleate formulation of claim 1, wherein the nutrient is one of calcium, magnesium, zinc, barium, or iron.
5. The nutrient-cochleate formulation of claim 1, wherein the nutrient is an amino acid.
6. The nutrient-cochleate formulation of claim 1, wherein the nutrient is a vitamin.
7. The nutrient-cochleate formulation of claim 6, wherein the vitamin is one of vitamin A, vitamin D, vitamin E, or vitamin K.
8. The nutrient-cochleate formulation of claim 2, wherein the nutrient is a fatty acid.
9. The nutrient-cochleate formulation of claim 1, wherein the nutrient is one of a saturated or a polyunsaturated fatty acid.
10. The nutrient-cochleate formulation of claim 1, wherein the nutrient is a saccharide.
11. The nutrient-cochleate formulation of claim 1, wherein the nutrient is a lipid.
12. The nutrient-cochleate formulation of claim 1, wherein the nutrient is a steroid.
13. A method of delivering a nutrient to a cell in a host comprising administering to said host a biologically effective amount of cochleatc fonmulation comprising:
   a) a nutrient component and
   b) a cochleate further comprising a negatively charged lipid component and a divalent cation component.
14. The method of claim 13, wherein the nutrient is one member selected from the group consisting of a mineral, an amino acid, a vitamin, a lipid, a fatty acid, and a saccharide.
15. The method of claim 13, wherein the nutrient is a mineral.
16. The method of claim 13, wherein the nutrient is one of calcium, magnesium, zinc, barium, or iron.
17. The method of claim 13, wherein the nutrient is an amino acid.
18. The method of claim 13, wherein the nutrient is a vitamin.
19. The method of claim 13, wherein the nutrient is one of vitamin A, vitamin D, vitamin E, or vitamin K.
20. The method of claim 13, wherein the nutrient is a fatty acid.
21. The method of claim 13, wherein the nutrient is a polyunsaturated fatty acid.
22. The method of claim 13, wherein the nutrient is a saccharide.
23. The method of claim 13, wherein the nutrient is a lipid.
24. The method of claim 13, wherein the nutrient is a steroid.
25. A cochleate formulation comprising:
   a) a soluble protein or soluble polypeptide and
   b) a cochleate further comprising a negatively charged lipid component and a divalent cation component.
26. The cochleate formulation of claim 25, wherein said polypeptide is a toxin.
27. The cochleate formulation of claim 25, wherein said polypeptide is a conjugated protein.

28. The cochleate formulation of claim 25, wherein said protein is a hormone.

29. A method of delivering a soluble protein or soluble polypeptide to a cell in a host comprising administering to said host a biologically effective amount of a cochleate formulation comprising:
 a) a soluble protein or soluble polypeptide and
 b) a cochleate further comprising a negatively charged lipid and a divalent cation component.

30. The method of claim 29, wherein the polypeptide is one of a toxin, a conjugated protein or a hormone.

31. A lipophilie drug-cochleate formulation comprising:
 a) a lipophilic drug and
 b) a cochleate further comprising a negatively charged lipid component and a divalent cation component.

32. The lipophilic drug-cochleate formulation of claim 31, wherein the drug is one of an anti-viral, an anesthetic, an anti-infectious, an anti-fungal, an anti-cancer, an immunosuppressant, a steroidal anti-inflammatory, a non-steroidal anti-inflammatory, a tranquilizer, a vasodilatory agent, a steroid, a microbicide or a metabolic poison.

33. The lipophilic drug-cochleate formulation of claim 31, wherein the drug is one of acyclovir, propanidid, propofol, alphadione, echinomycine, miconazole nitrate, teniposide, vitamin B, hexamethylmelamine, taxol, taxotere, melphalan, adriamycin, cyclosporine A, 18-hydroxydeoxycorticosterone, rapamycine, prednisolone, dexamethazone, cortisone, hydrocortisone, pyroxicam, naproxen, diazepam, verapamil, or nifedipine.

34. A method of delivering a lipophilic drug to a cell in a host comprising administering to said host a biologically effective amount of a cochleate formulation comprising:
 a) a lipophilic drug component and
 b) a cochleate further comprising a negatively charged lipid component and a divalent cation component.

35. The method of claim 34, wherein the lipid soluble drug is one of an anti-viral, an anesthetic, an anti-infectious, an anti-fungal, an anti-cancer, an immunosuppressant, a steroidal anti-inflammatory, a non-steroidal anti-inflammatory, a tranquilizer, a vasodilatory agent, a steroid, a microbicide or a metabolic poison.

36. The method of claim 34, wherein the drug is one of acyclovir, propanidid, propofol, alphadione, echinomycine, miconazole nitrate, teniposide, vitamin B, hexamethylmelamine, taxol, taxotere, melphalan, adriamycin, cyclosporine A, 18-hydroxydeoxycorticosterone, rapamycine, prednisolone, dexamethazone, cortisone, hydrocortisone, pyroxicam, naproxen, diazepam, verapamil, or nifedipine.

37. A pigient-cochleate formulation comprising:
 a) a pigment and
 b) a cochleate further comprising a negatively charged lipid component and a divalent cation component.

38. A method of delivering a pigment to a cell in a host comprising administering to said host a biologically effective amount of a cochleate formulation comprising:
 a) a pigment and
 b) a cochleate further comprising a negatively chargced lipid component and a divalent cation component.

39. A metal-cochleate formulation comprising:
 a) a metal and
 b) a cochleate further comprising a negatively charged lipid component and a divalent cation component.

40. The metal-cochleate formulation of claim 39, wherein the metal is one of $Fe^{+2}$, $Zn^{+2}$, $Cu^{+2}$, or $Mg^{+2}$.

41. A method of delivering a metal to a cell in a host comprising administering to said host a biologically effective amount of a cochleate formulation comprising:
 a) a metal and
 b) a cochleate further comprising a negatively charged lipid component and a divalent cation component.

42. The method of claim 41, wherein the metal is one of $Fe^{+2}$, $Zn^{+2}$, $Cu^{+2}$, or $Mg^{+2}$.

43. A compound with a multi-ring structure-cochleate formulation comprising:
 a) a compound with a multi-ring structure and
 b) a cochleate further comprising a negatively charged lipid component and a divalent cation component.

44. A method of administering a compound with a multi-ring structure to a cell in a host comprising administering to said host a biologically effective amount of a cochleate formulation comprising:
 a) a compound with a multi-ring structure and
 b) a cochleate further comprising a negatively charged lipid component and a divalent cation component.

45. A saccharide-cochleate formulation comprising:
 a) a saccharide and
 b) a cochleate further comprising a negatively charged lipid component and a divalent cation component.

46. The saccharide-cochleate formulation of claim 45, wherein the saccharide is starch.

47. A method of administering a saccharide to a cell in a host comprising administering to said host a biologically effective amount of a cochleate formulation comprising:
 a) a saccharide and
 b) a cochleate further comprising a negatively charged lipid component and a divalent cation component.

48. The method of claim 47, wherein the saccharide is starch.

49. An enzyme-cochleate formulation comprising:
 a) an enzyme and
 b) a cochleate further comprising a negatively charged lipid component and a divalent cation component.

50. A method of administering an enzyme to a cell in a host comprising administering a biologically effective amount of a cochleate formulation comprising:
 a) a enzyme and
 b) a cochleate further comprising a negatively charged lipid component and a divalent cation component.

51. A co-factor-cochleate formulation comprising:
 a) a co-factor and
 b) a cochleate further comprising a negatively charged lipid component and a divalent cation component.

52. A method of administering a co-factor to a host comprising administering to said host a biologically effective amount of a cochleate formulation comprising:
 a) a co-factor and
 b) a cochleate further comprising a negatively charged lipid component and a divalent cation component.

53. An adjuvant-cochleate formulation comprising:
 a) an adjuvant and
 b) a cochleate further comprising a negatively charged lipid component and a divalent cation component.

54. A method of administering an adjuvant to a host comprising administering to said host a biologically effective amount of a cochleate formulation comprising:
 a) an adjuvant and
 b) a cochleate further comprising a negatively chargced lipid component and a divalent cation component.

55. A method of delivering a biologically relevant molecule to a cell comprising contacting said cell with a cochleate formulation comprising:
   a) at least one biologically relevant molecule component and
   b) a cochleate further comprising a negatively charged lipid component and a divalent cation component.

56. A method of delivering a biologically relevant molecule to a host comprising topically applying to said host a biologically effective amount of a cochleate formulation comprising:
   a) at least one biologically relevant molecule component and
   b) a cochleate further comprising a negatively charged lipid component and a divalent cation component.

57. A flavor-cochleate formulation comprising:
   a) at least one flavor, and
   b) a cochleate further comprising at least one negatively charged lipid component, and at least one divalent cation component.

58. The flavor-cochleate formulation of claim 57, wherein the flavor is one member selected from the group consisting of essential oils and extracts.

59. The flavor-cochleate formulation of claim 58, wherein the essential oil is cinnamon oil.

* * * * *